United States Patent [19]

South et al.

[11] Patent Number: 5,616,789

[45] Date of Patent: Apr. 1, 1997

[54] HYDRAZINECARBOXYLIC ACIDS

[75] Inventors: Michael S. South; Terri L. Jakuboski, both of St. Louis, Mo.

[73] Assignee: Monsanto Company, St. Louis, Mo.

[21] Appl. No.: 471,595

[22] Filed: Jun. 6, 1995

Related U.S. Application Data

[62] Division of Ser. No. 320,996, Oct. 11, 1994.

[51] Int. Cl.⁶ .................................................. A01N 33/26
[52] U.S. Cl. ............................................. 562/439; 560/34
[58] Field of Search ............................ 562/440, 439; 560/34

[56] References Cited

U.S. PATENT DOCUMENTS

| | | | |
|---|---|---|---|
| 4,387,104 | 6/1983 | Heerdt et al. | ............................ 562/439 |
| 4,623,376 | 11/1986 | Speltz | ........................................ 544/238 |
| 5,233,047 | 8/1993 | MacLeay | ................................ 562/439 |

FOREIGN PATENT DOCUMENTS

| | | |
|---|---|---|
| 026040 | 4/1981 | European Pat. Off. . |
| 2615188 | 11/1988 | France . |
| 3624349 | 1/1988 | Germany . |
| WO91/17983 | 11/1991 | WIPO . |

OTHER PUBLICATIONS

Auer et al., *Environ. Qual. Saf, Suppl.* (1975), pp. 680–685 "The Chemistry and Properties of New and Herbicidal Derivatives of 3-Phenylpyridazine".

*Primary Examiner*—Donald G. Daus
*Attorney, Agent, or Firm*—Grace L. Bonner

[57] ABSTRACT

Disclosed are certain 3-phenylpyridazines, compositions thereof which are herbicidal and methods of using such compositions for controlling undesired plants. Intermediates useful in preparing the 3-phenylpyridazines are disclosed.

1 Claim, No Drawings

HYDRAZINECARBOXYLIC ACIDS

This application is a divisional of U.S. Ser. No. 08/320,996 filed Oct. 11, 1994, now pending.

FIELD OF THE INVENTION

The present invention relates to novel compounds useful for controlling undesired plants and for retarding plant growth. More particularly, the present invention relates to certain 3-phenylpyridazines useful for controlling undesired plants and for retarding plant growth.

PRIOR ART

In U.S. Pat. No. 4,623,376, certain substituted 3-phenylpyridazines have been disclosed as being useful as herbicides.

In Auer et al, "The Chemistry and Properties of New and Herbicidal Derivatives of 3-Phenylpyridazine", *Environ. Qual. Saf. Suppl.*, (1975), pp 680–685, certain substituted 3-phenylpyridazines have been disclosed as being useful as herbicides.

There is a continuing need in the art for herbicides which provide a broad spectrum of control of weeds and which may be better tolerated by crops. The present invention produces such kind of improved and useful herbicides.

SUMMARY OF THE INVENTION

The novel compounds of the present invention may be depicted by the following structural formula (W):

wherein:

A and E are each hydrogen;

B and D are each independently hydrogen, $C_1$–$C_3$ haloalkyl, $C_1$–$C_3$ haloalkyl, nitro, amino, halo, $C_1$–$C_7$ alkylsilyl, $C_1$–$C_7$ alkyl, $C_1$–$C_7$ haloalkoxy, phenyl $C_1$–$C_7$ alkylsilyl, or halo $C_1$–$C_7$ alkylthio;

C is hydrogen, nitro or amino;

F is hydrogen, halo, $C_1$–$C_7$ alkoxy, hydroxy, $C_1$–$C_7$ alkyl, $C_1$–$C_7$ alkynyl, $C_1$–$C_7$ alkenyl, $C_1$–$C_7$ alkylthio, $C_1$–$C_7$ alkylamino, $C_1$–$C_7$ alkylsulfonyl, or $C_1$–$C_7$ alkylsulfinyl;

G is hydrogen, hydroxycarbonyl, hydroxycarbonylamino, amino, halo, $C_1$–$C_7$ alkyl, cyanothio, thio, formylamino, $C_1$–$C_7$ alkylamino, $C_1$–$C_7$ alkoxy, $C_1$–$C_7$ alkylamino, $C_1$–$C_7$ alkylthio, $C_1$–$C_7$ alkynloxy, $C_1$–$C_7$ alkenyloxy, hydroxy, hydroxycarbonyl $C_1$–$C_7$ alkoxy, halo $C_1$–$C_7$ alkylthio, $C_1$–$C_7$ alkoxy $C_1$–$C_7$ alkoxy, $C_1$–$C_7$ alkoxy $C_1$–$C_7$ alkoxy $C_1$–$C_7$ alkoxy, aminocarbonyl, $C_1$–$C_7$ alkylthio $C_1$–$C_7$ alkoxy, $C_1$–$C_7$ alkylaminooxy, $C_1$–$C_7$ alkylcarbonylamino, halo $C_1$–$C_7$ alkoxy, aminocarbonyl, $C_1$–$C_7$ alkylsulfinyl, $C_1$–$C_7$ alkylsulfonyl, $C_1$–$C_7$ alkoxycarbonylamino, $C_1$–$C_7$ alkylaminocarbonylamino, $C_1$–$C_7$ alkylthio, cyano, $C_1$–$C_7$alkoxy, or $C_1$–$C_7$ alkylaminocarbonylamino; and H is hydrogen, halo, $C_1$–$C_7$ alkoxy $C_1$–$C_7$ alkylthio, $C_1$–$C_7$ alkyl, $C_1$–$C_7$ alkynyl, $C_1$–$C_7$ alkenyl, $C_1$–$C_7$ alkylamino, hydroxy, $C_1$–$C_7$ alkylsulfinyl, $C_1$–$C_7$ alkylsulfonyl, or cyano;

Either nitrogen of the pyridazine ring may be substituted with an oxide. G and H together may form a 5-member hetero oxygen ring. Herbicidal salts and esters of the compounds are also included.

The present invention provides novel compounds of the general Formula W depicted above which exhibit desirable herbicidal properties and further provides herbicidal compositions for the selective controlling of weeds in crop plants. The compositions comprise one or more compounds of Formula W herein by themselves or admixed with one or more carriers, such as solid and/or liquid inert extenders or diluents and/or wetting agents and optionally other active herbicides, insecticides, growth regulators, plant nutrients and like additaments. The invention also provides an effective method of controlling undesirable plants, such as grasses, perennial and annual broad-leafed weeds and so on which comprises applying to the locus of the plants to be controlled on herbicidally effective amount of at least one 3-phenylpyridazine compound.

These novel 3-phenylpyridazine compounds which may be employed as an active ingredient in this invention can be prepared by a variety of processes such as one of the general procedures as will be described below.

The present invention also provides new and useful processes for making 3-phenylpyridazine compounds and intermediates thereof.

DETAILED DESCRIPTION OF THE INVENTION

It has been shown that the phenyl substituted pyridazine compounds within the above depicted general Formula W are not only herbicidal but also have good herbicidal tolerance by certain crop plants, especially corn. The preferred compounds herein provide a broader spectrum of weed control and show good perennial broad-leaf activity. The field soil half-life of the preferred compounds provide longer residual control than alachlor but is normally short enough that any carryover problems are environmentally acceptable.

In this specification and claims, numerical values are not critical unless otherwise stated. That is, the numerical values may be read as if prefaced with the word "about" or "substantially".

The following defines the various terms used in the application.

The term "$C_1$–$C_7$ alkyl" or in the shortened cognate form "$C_1$–$C_7$ alk" as used herein include the straight and branched aliphatic groups of one to ten carbon atoms, such as methyl, ethyl, propyl, isopropyl (1-methyl-ethyl), butyl, isobutyl (2-methylpropyl), sec-butyl, (1-methylpropyl), tert-butyl, (1,1-dimethylethyl), pentyl, isopentyl, (3-methylbutyl), sec-pentyl (1-methylbutyl), 1,1-dimethylpropyl, 1-2-dimethylpropyl, neopentyl, (2,2-dimethylpropyl), hexyl, isohexyl (4-methylpentyl), sec-hexyl, (1-methylpentyl), 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, and the like. The terms, such as "$C_1$–$C_3$" and "$C_1$–$C_5$" are included in the term $C_1$–$C_{10}$ but with a corresponding lesser number of carbon atoms as indicated.

The term "$C_1$–$C_3$ haloalkyl" as used herein includes such radicals as trifluoromethyl, trichloromethyl, difluoromethyl, chlorodifluoromethyl, fluoromethyl, bromomethyl, α,α-difluoromethyl, pentafluoroethyl, heptafluoro-n-propyl, pentachloroethyl, iodomethyl, etc., where the number of carbon atoms in the alkyl is 1–3, inclusive.

The term "halogen" either alone or in compound words such as "haloalkyl" denotes fluorine, chlorine, bromine or iodine.

The term "alkoxy" denotes methoxy, ethoxy, n-propyloxy, isopropyloxy and the different butoxy, pentoxy, hexyloxy isomers, etc.

The term "alkenyl" denotes straight or branched alkenes, e.g., vinyl, 1-propenyl, 2-propenyl, 3-propenyl and the different butenyl, pentenyl, hexenyl isomers, etc.

The term "alkynyl" denotes straight chain or branched alkynes, e.g., ethynyl, 1-propynyl, 3-propynyl, etc., including the different butynyl, pentynyl and hexynyl isomers.

The term "alkylthio" denotes methylthio, ethylthio and the various propylthio, butylthio, pentylthio and hexylthio isomers.

Alkylsulfinyl, alkylsulfonyl, alkylamine, etc., are defined analogously to above terms as will be understood by those skilled in the art.

Processes for preparing the compounds of the present invention are disclosed in the schematic diagrams and written descriptions which follow below.

The compounds which can be prepared by the new and useful process of the present invention include those of the following general formula (W'):

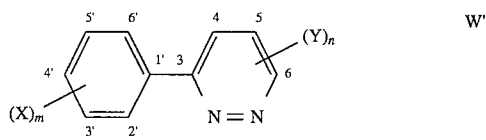

In broad aspect, the preferred overall process for preparing the compounds of Formula W' is best viewed in the separate process steps required to prepare the necessary intermediates, immediate precursors and end products of the above formula. The products of. "Processes I, III and IV", provide the intermediates necessary for "Processes II and V". The compounds according to Formula W' are prepared by either a single process "I, II, or V" or any suitable combination of "Processes I–V". It is expressly understood that various modifications obvious to those skilled in the art are contemplated. Specific embodiments of the preparation of the compounds herein are described in Examples 1–19 below.

In the sequence of process steps described below, the various symbols defining radical substituents and the number of such substituents, e.g., X, Y, Z, m, n, $R_1$–$R_7$, etc., have the same meaning as defined for the compounds of Formula W and compounds related thereto, unless otherwise qualified or limited. The symbol m is zero or an integer of 1–5, inclusive, and n is zero or an integer of 1–3, inclusive. X is selected from substituents A, B, C, D and E as above defined and Y is selected from substituents F, G and H as above defined.

Process I

This process describes the preparation of compounds of Formula E of the following schematic which in many cases are equivalent to compounds of Formula W'. Process I also describes the preparation of important intermediate compounds of Formula E, which are useful for the preparation of compounds of Formula W'. X is a substituent including A–E radicals as above defined; Y is a substituent including F–H radicals as above defined. The subscript m is zero or an integer of 1–4; subscript n is zero or an integer of 1–3.

The first step of Process I involves the conversion of acetophenones of Formula A, which are either known in the art, commercially available, or whose preparation is described herein, to hydrazones of Formula B. The reaction is carried out by admixing the aCetophenone with ethyl carbazate in the presence of a catalytic amount of an acid chosen from p-toluenesulfonic acid, sulfuric acid, methanesulfonic acid or the like in any anhydrous solvent or mixture of solvents with the preferred solvents being chosen from benzene, toluene, ether, tetrahydrofuran, or methylene chloride. This is followed by removal of the water that is generated with a drying agent, such as sodium sulfate, magnesium sulfate, or molecular sieves or by refluxing the mixture over a "Dean-Stark" trap. The reaction temperature may range from 0° C. to 150° C., preferably 25° C. to 120° C. The reaction time may vary from a few minutes to several weeks depending on the selected reagents, the amounts of the reagents, reaction temperature, etc. The compounds of Formula B are isolated by removal of the reaction solvent followed by recrystallization from an appropriate inert organic solvent.

Scheme 1

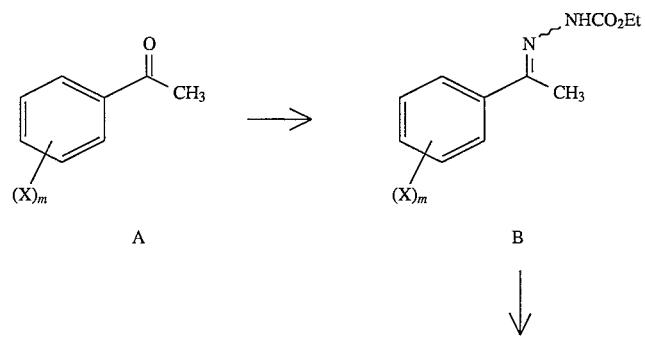

-continued
Scheme 1

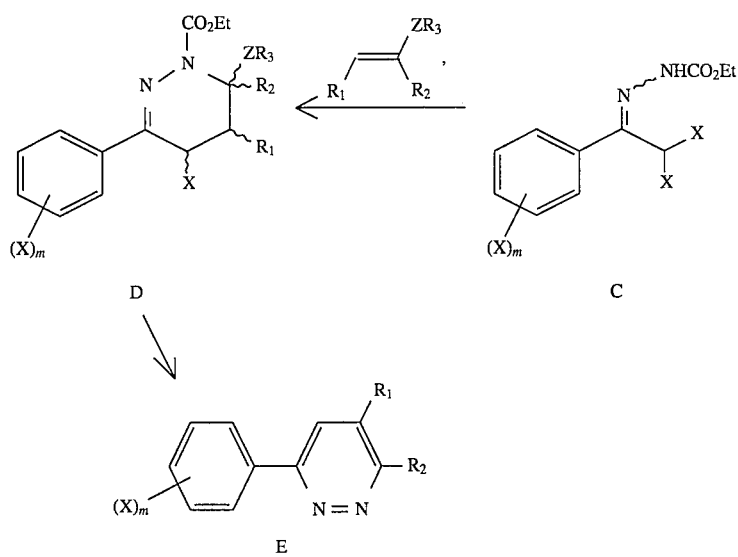

The second step in Process I involves the conversion of hydrazones of Formula B to dichlorohydrazones of Formula C by treatment with a suitable chlorinating agent, preferably chosen from N-chlorosuccinimide, sulfuryl chloride, oxalyl chloride, thionyl chloride, 1,3-dichloro-5,5-dimethylhydantoin, chlorine gas, or trichlorotriazinone. The reaction can be carried out in any nonreactive solvent or mixture of solvents, preferably carbon tetrachloride, chloroform, methylene chloride, or dichloroethane. The reaction temperature may range from −78° C. to 150° C., preferably −20° C. to 100° C. The reaction period may be chosen from a few minutes to several weeks depending on the amounts of reagents, reaction temperature, etc. The resulting reaction mixture containing the compounds of Formula C are filtered and then concentrated and may be used as is or recrystallized from an appropriate solvent.

The third step in Process I involves the conversion of compounds of Formula C to compounds of Formula D by treatment of compounds of Formula C with a hindered amine base, preferably chosen from triethylamine, diisopropylethylamine, tributylamine, DBU or DBN and an electron rich enamine or enol ether (electron rich olefins). The electron rich olefins depicted in Scheme I are either known in the art or are prepared as described herein from an appropriate ketone, aldehyde, or acetylene and may have $ZR_3$ equal to morpholine, methoxy, or ethoxy and $R_1$ and/or $R_2$ equal to hydrogen, lower alkyl or haloalkyl, methoxy, or carboxylate. The reaction may be carried out in any anhydrous solvent or mixtures of solvents, which includes preferably methylene chloride, tetrahydrofuran, chloroform, carbontetrachloride, dichloroethane, or benzene. The reaction temperature may range from −78° C. to 150° C., preferably −20° C. to 100° C. The reaction period may be chosen from a few minutes to several weeks depending on the selected reagents, the amounts of the reagents, reaction temperature, etc. The resulting reaction mixture containing the compounds of Formula D is then diluted with water and extracted several times with an appropriate organic solvent. The organic solvent is then dried, filtered and evaporated in vacuo. The resulting compounds of Formula D are then purified by standard methods, such as crystallization or chromatography and are usually isolated as a mixture of one or more diastereomers.

The fourth step in Process I involves the conversion of compounds of Formula D to compounds of Formula E by treatment with a base preferably chosen from NaOH, KOH, t-BuOK, NaOMe, NaOEt, or LDA or by heating the compounds of Formula D at an elevated temperature in a appropriate solvent. The reaction may be performed in any appropriate solvent, preferably chosen from methanol, ethanol, THF, DMSO or DMF. The reaction temperature may range from −78° C. to 150° C., preferably −20° C. to 100° C. The reaction period may be chosen from a few minutes to several weeks depending on the selected reagent, the amounts of the reagents, reaction temperature, etc. The reaction mixture containing the compounds of Formula E is then diluted with water, made acidic, and then extracted with an appropriate organic solvent. The organic solvent is then dried, filtered and evaporated in vacuo. The resulting compounds of Formula E are then used as is or are purified by standard methods, such as crystallization or chromatography.

Process II

This process describes the preparation of compounds of Formulas G–L inclusive, which are depicted below and are included in the compounds of Formula W'.

The first step in Process II involves the conversion of compounds of Formula F–G inclusive where $R_4$ is OH or $NH_2$. When $R_4$ is OH the compounds of Formula F are treated with diphenylphosphorylazide, an organic base most preferably chosen from triethylamine, DBU or N,N-diisopropylethylamine. The reaction may be carried out in any suitable alcoholic solvent, such as methanol, ethanol, t-butanol or i-propanol. The reaction temperature may range from 25° C. to 100° C., preferably 75° C. to 80° C.

Scheme 2

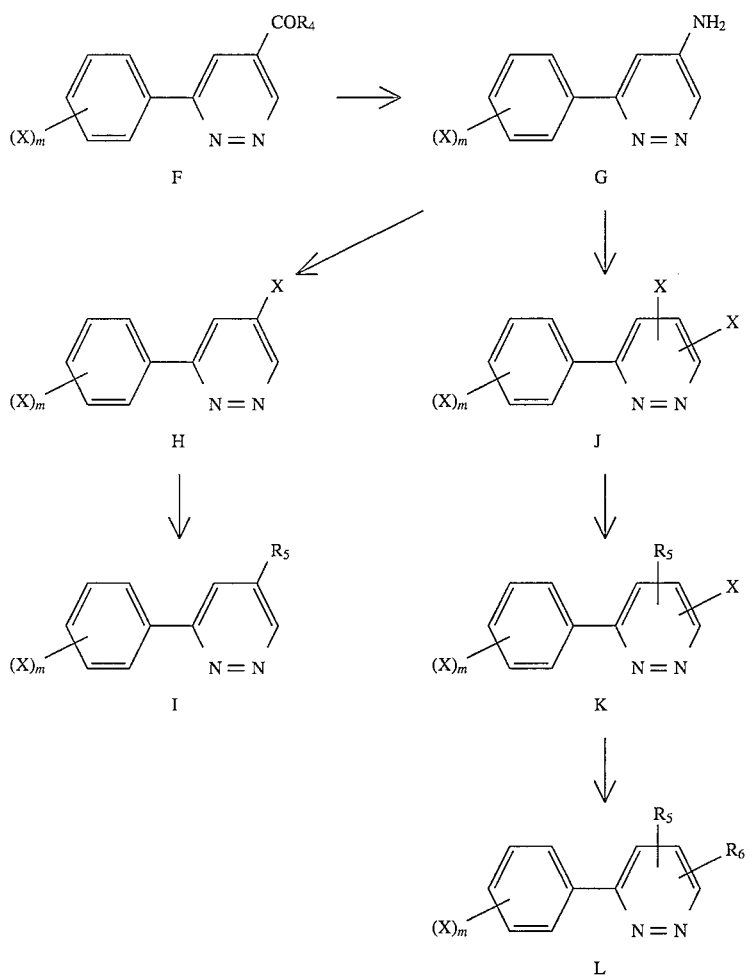

The reaction time may range from a few minutes to several weeks depending on the selected reagents, the reaction temperature, amounts of the reagents, etc. The intermediate carbamate that is formed is converted to compounds of Formula G by removal of the above mentioned alcoholic solvent in vacuo followed by stirring the mixture in an aqueous acid chosen from hydrochloric acid, sulfuric acid, nitric acid, or acetic acid. The reaction temperature may range from 25° C. to 100° C., preferably 50° C. to 100° C. The reaction time may range from a few minutes to several weeks depending on the selected reagents, the reaction time, amount of the reagents, etc. The compounds of Formula G are isolated by neutralizing the aqueous acid solution with a base followed by extraction with an appropriate organic solvent. The organic solvent is removed in vacuo and the compounds of Formula G are purified by standard methods, such as recrystallization or chromatography.

In the first step of Process II when $R_4$ is $NH_2$, the compounds of Formula F are treated with an aqueous sodium hypochlorite solution in the presence of a base such as potassium carbonate, sodium hydroxide, or potassium hydroxide. The reaction temperature may range from 25° C. to 100° C. The reaction time may vary from a few minutes to several weeks depending on the selected reagents, the amounts of the reagents, reaction temperature, etc. The compounds of Formula G are isolated by extraction of the aqueous solution with an appropriate organic solvent followed by evaporation in vacuo. The compounds of Formula G may be purified by standard methods, such as recrystallization or chromatography.

The second step of Process II involves the conversion of compounds of Formula G–H, inclusive, by treatment of G with an alkylnitrite and a halogenating reagent such as $CuX_2$, CuX or $X_2$. In these cases X=Cl, Br or I. The reaction may be carried out in any anhydrous organic solvent or mixture of solvents, preferably THF, chloroform, methylene chloride, acetonitrile or dimethoxyethane. The reaction temperature may range from –20° C. to 100° C., preferably 40° C. to 75° C. The reaction time may range from a few minutes to several weeks depending on the selected reagents, the reaction temperature, amounts of reagents, etc. The compounds of Formula H are isolated by pouring the reaction mixture into dilute aqueous acid followed by extraction with an organic solvent which is dried, filtered and evaporated in vacuo. The compounds of Formula H may be purified by standard methods, such as crystallization or chromatography.

The third step in Process II involves the conversion of compounds of Formulas H and I by treatment of H with an alkyl alcohol, thiol or amine and a base, preferably chosen from KOH, NaOH, NaH, $K_2CO_3$, LDA or t-BuOK. The reaction may be carried out in any anhydrous solvent or mixture of solvents, preferably the neat alkyl alcohol, thiol, amine, THF, DMF, DMSO, or di-methoxyethane. The reaction temperature may vary from −78° C. to 150° C., preferably −20° C. to 100° C. The reaction time may vary from several minutes to several weeks depending on the amounts of the reagents, reaction temperatures, etc. The compounds of Formula I are isolated by pouring the mixture into water and extracting with an organic solvent. The compounds of Formula I are purified after removal of the organic solvent in vacuo by standard methods, such as recrystallization or chromatography.

The fourth step in Process II involves the conversion of compounds of Formula G–J, inclusive, where X is in the 5- and the 6-positions of the pyridazine of Formula J or X is in the 4- and the 5-positions of the pyridazine of Formula J.

To prepare compounds of Formula J where X is in the 5- and the 6-positions of the pyridazine, compounds of Formula G are first converted to compounds of Formula H as described above. The compounds of Formula H are then treated with a peracid, preferably chosen from m-chloroperbenzoic acid, peracetic acid, trifluoroperacetic acid or hydrogen peroxide to give an intermediate 1-pyridazine N-oxide. The reaction solvent may be chosen from any inert organic solvent, preferably chloroform, benzene or methylene chloride. The reaction temperature may vary from −20° C. to 100° C., preferably 25° C. to 80° C. The reaction time may vary from a few minutes to several weeks depending on the reaction temperature, amounts of the reagents, etc. The N-oxide may be isolated by pouring the reaction mixture into water and extracting with an appropriate organic solvent. After the solvent is removed in vacuo the product may be purified by standard methods, such as recrystallization or chromatography. The N-oxide is then treated with a halogenation reagent, preferably chosen from $POX_3$, $SOX_2$, $SO_2X_2$, $PX_5$, $PX_3$ or $(CO)_2X_2$. The reaction is done neat with the halogenation reagent as a solvent or preferably in a solvent chosen from benzene, chloroform, methylene chloride or carbon tetrachloride. The reaction temperature may vary from −20° C. to 100° C., preferably 25° C. to 80° C. The reaction time may vary from a few minutes to several weeks depending on the reaction temperature, amounts of the reagents, etc. The compounds of Formula J where X is in the 5- and the 6-positions of the pyridazine are isolated by removal of the solvent in vacuo followed by purification by standard methods, such as recrystallization or chromatography.

To prepare compounds of Formula J where X is in the 4- and the 5-positions of the pyridazine, compounds of Formula G are treated with a halogenation reagent chosen from N-halosuccinimide, $X_2$, 1,3-dihalo-4,4-dimethylhydantoin, $SO_2X_2$ or $(CO)_2X_2$. The reaction may be performed in any nonreactive organic solvent or mixtures of solvents, preferably acetonitrile, chloroform, methylene chloride or benzene. The reaction temperature may vary from −20° C. to 100° C., preferably 25° C. to 80° C. The reaction time may vary from a few minutes to several weeks depending on the reaction temperature, amounts of the reagents, etc. The intermediate 4-halo-5-aminopyridazine may be isolated by removal of volatiles in vacuo followed by purification by standard methods, such as recrystallization or chromatography. The intermediate 4-halo-5-aminopyridazine is then converted to compounds of Formula J where X is in the 4- and the 5-positions of the pyridazine by the same procedure described above for the preparation of compounds of Formula H.

The fifth step in Process II involves the conversion of compounds of Formulas J to K or L by treatment of compounds of Formula J with either one or two equivalents of an alkyl alcohol, thiol or amine and a base. In these sequences $R_5$ and $R_6$ may be the same or different depending on the nucleophile utilized for the reaction. The procedure for the conversion of J to either K or L is identical to that utilized for preparation of compounds of Formula I.

The sixth step in Process II involves the conversion of compounds of Formula K to compounds of Formula L by treatment of compounds of Formula K with a tetraalkyl tin reagent, preferably chosen from tetramethyltin or vinyltributyltin and a palladium catalyst, such as bis(triphenylphosphine)palladium(II) chloride or trans-benzyl(chloro)bis-(triphenylphosphine)palladium(II). The reaction may be performed in any suitable anhydrous inert organic solvent or mixture of solvents, preferably DMF, DMSO, dimethoxyethane, benzene or toluene. The reaction temperature may vary from 0° C. to 150° C., preferably 25° C. to 100° C. The reaction time may vary from a few minutes to several weeks depending on the reaction temperature, amounts of the reagents, etc. The compounds of Formula L are isolated by pouring the reaction mixture into water followed by extraction with a suitable organic solvent. The solvent is then dried and evaporated in vacuo to give the compounds of Formula L which may be purified by standard methods, such as recrystallization or chromatography.

Process III

This process involves the preparation of important intermediate compounds of Formula R which are useful in the overall process scheme for producing compounds of Formula W.

The first step in the process for the preparation of compounds of Formula R proceeds from 3,4-dichloro-3-hydroxypyridazine M, which is commercially available and known in the art. Treatment of compounds of Formula M with an appropriate protecting group chosen preferably from chloromethylmethyl ether, chloromethylthiomethyl ether, dihydropyran or 2-methoxyethoxymethyl chloride and an organic or inorganic acid, such as p-toluenesulfonic acid or sulfuric acid or a base chosen from triethylamine or N,N-diisopyropylethylamine gives a compound of Formula N. In compounds of Formula N, $R_7$ is derived from one of the protecting groups mentioned above. The reaction can be carried out in any anhydrous solvent or mixture of solvents with the preferred solvents being chosen from ether, tetrahydrofuran, benzene, toluene or methylene chloride. The reaction temperatures may range from −78° C. to 150° C., preferably 0° C. to 100° C. The reaction period may be chosen from a few minutes to several weeks depending on the selected reatents, the amounts of reagents, reaction temperature, etc. After the reaction is complete, the mixture containing the compounds of Formula N are diluted with an appropriate organic solvent and extracted with an aqueous base such as sodium bicarbonate. The compounds of Formula N are isolated by drying the organic solvent, filtration and then removal of the solvent in vacuo. The compounds of Formula N are utilized as is or if necessary the product is purified by standard methods, such as crystallization or column chromatography.

The second step in Process III involves the conversion of compounds of Formula N-O, inclusive, by treatment of N with an alkyl alcohol, thiol, or amine and an appropriate base, such as sodium hydroxide, potassium hydroxide, sodium hydride, potassium hydride, sodium bicarbonate, potassium carbonate, triethyl amine, N,N-diisopyropylethylamine or DBU to give compounds of Formula O.

Scheme 3

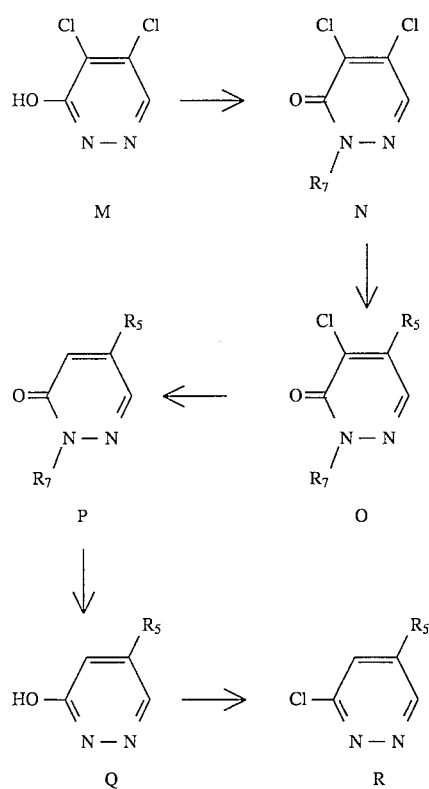

In compounds of Formula O, $R_5$ is derived from the alkyl alcohol, thiol or amine mentioned above and in many cases would be equivalent to $Y_n$ of Formula W'. The reaction can be carried out neat with the above mentioned alcohol, thiol or amine as solvent or in any suitable anhydrous solvent or mixture of solvents with the preferred solvents being chosen from ether, tetrahydrofuran, benzene, N,N-dimethylformamide or dimethylsulfoxide. The reaction temperatures may range from −78° C. to 150° C., preferably −20° C. to 100° C. The reaction period may be chosen from a few minutes to several weeks depending on the amounts of reagents, reaction temperature, etc. The mixture containing the compounds of Formula O are then diluted with an organic solvent and extracted several times with water. The compounds of Formula O are isolated by removal of the organic solvent in-vacuo and may be used as is or if necessary may be purified by standard methods, such as crystallization or column chromatography.

The third step in Process III involves the conversion of compounds of Formula O to compounds of Formula P by treatment of compounds of Formula O with hydrogen, an appropriate transition metal catalyst, such as Pd-C, Pt-C, or $PtO_2$, and an appropriate base such as triethyl amine, N,N-diisopyropylethylamine, or DBU to give compounds of Formula P. The reaction can be carried out in any anhydrous solvent or mixture of solvents with the preferred solvents being chosen from methanol, ethanol, benzene, or ethyl acetate, preferably methanol or ethanol. The reaction temperatures may range from −78° to 150° C., preferably 0° C. to 40° C. The reaction period may be chosen from a few minutes to several weeks depending on the selected reagents, the amounts of reagents, reaction temperature, etc. The compounds of Formula P are isolated by filtration and removal of the solvent in vacuo. The compounds of Formula P are used as is or may be purified by standard methods, such as crystallization or column chromatography.

The fourth step in Process III involves the conversion of compounds of Formula P to compounds of Formula Q by treatment of P with an aqueous acid, such as hydrochloric acid, phosphoric acid, sulfuric acid, or nitric acid to give compounds of Formula Q. The reaction is carried out in the aqueous acid as solvent in the presence of a co-solvent, such as methanol, ethanol or tetrahydrofuran with the reaction temperatures ranging from 0° C. to 100° C., preferably 25° C. to 100° C. The reaction period may be chosen from a few minutes to several weeks depending on the selected reagents, the amounts of reagents, reaction temperature, etc. The compounds of Formula Q are isolated by making the reaction mixture basic with sodium hydroxide, extracting with a chlorinated solvent, such as methylene chloride, chloroform, or carbon tetrachloride to remove contaminants, then acidifying with concentrated acid to precipitate the product. The products of Formula Q are then collected by filtration and dried and may be used as is or if necessary purified by standard methods, such as crystallization or column chromatography.

The fifth step in Process III involves the conversion of compounds of Formula Q to compounds of Formula R by treatment of compounds of Formula Q with a chlorinating agent, such as thionyl chloride, oxalyl chloride, sulfuryl chloride or phosphorous oxychloride to give compounds of Formula R. The reaction is carried out neat in the chlorinating agent as solvent or with the chlorinating agent and a co-solvent, such as methylene chloride, chloroform or carbon tetrachloride. The reaction temperature may range from 0° C. to 100° C., preferably 25° C. to 100° C. The reaction period may be chosen from a few minutes to several weeks depending on the selected reagents, the amounts of reagents, reaction temperature, etc. The compounds of Formula R are isolated by removal of the solvents in vacuo to give the products which can be used as is or purified by standard methods, such as crystallization or column chromatography.

Process IV

This process describes the preparation of important intermediate compounds of Formula T which are useful in the overall process scheme for producing compounds of Formula W.

Scheme 4

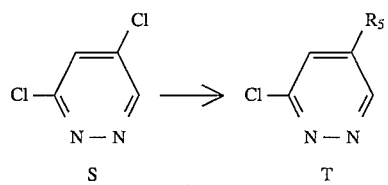

The first step of Process IV involves the conversion of 3,5-dichloropyridazine S, which is known in the art (W. Deinhammer et al., German Patent No. 2,706,701), to compounds of Formula T by treatment with one equivalent of an alkyl alcohol, thiol, or amine and an appropriate base such as sodium hydroxide, potassium hydroxide, sodium hydride, potassium hydride, sodium bicarbonate, potassium carbonate, triethyl amine, N,N-diisopropylethylamine or DBU. In compounds of Formula T, $R_5$ is derived from the alkyl alcohol, thiol, or amine mentioned above and in many cases can be equivalent to Yn of Formula W. The reaction can be carried out neat with the above mentioned alcohol, thiol, or amine as solvent or in any anhydrous solvent or mixture of solvents with the preferred solvents being chosen from ether, tetrahydrofuran, benzene, N,N-di-methylformamide, or dimethylsulfoxide. The reaction temperatures may range from −78° C. to 150° C., preferably −20° C. to 100° C. The reaction period may be chosen from a few minutes to several weeks depending on the selected reagents, the amounts of reagents, reaction temperature, etc. The mixture containing the compounds of Formula T are then diluted with an organic solvent and extracted several times with water. The compounds of Formula T are isolated by removal of the organic solvent in vacuo and may be used as is or if necessary may be purified by standard methods, such as crystallization or column chromatography.

Process V

This process describes the preparation of compounds of Formula W from compounds of Formulas U and V.

Scheme 5

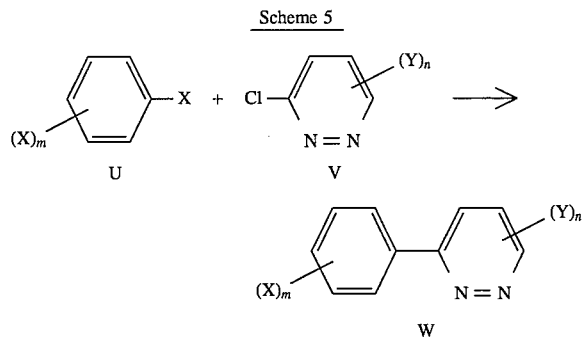

compounds of Formula U which are either known in the art, commercially available, or prepared as described herein are treated with magnesium metal or a palladium(0) catalyst followed by a tin reagent in an appropriate solvent, preferably chosen from ether, THF, toluene, or dimethoxyethane to generate a "Grignard Reagent" or an "organotin reagent". To this is added a transition metal catalyst, preferably chosen from bis(triphenylphosphine)nickel(II) chloride, 1,2-bis-(diphenylphosphinoethane)nickel(II) chloride, or tetrakis(triphenylphosphine)palladium(0) and compounds of Formula V. The mixture is allowed to react at a temperature from −20° C. to 100° C., preferably 0° C. to 80° C. The reaction period may be chosen from a few minutes to several weeks depending on the amounts of reagents, reaction temperature, etc. The mixture containing the compounds of Formula W are then poured into water and extracted with an appropriate organic solvent. After drying, the solvent is removed in vacuo to give the compounds of Formula W which can be purified by standard methods, such as recrystallization or chromatography.

The acid addition salts useful in the present composition can be prepared by admixing a suitable compound of Formula W with a suitable acid to form the corresponding acid addition salt. Examples of those acids which may be employed include inorganic acids, such as hydrochloric acid, sulfuric acid, nitric acid, phosphoric acid and an organic acid, such as trichloroacetic acid. It is to be noted that certain compounds of Formula W may not be converted conveniently to a corresponding suitable acid addition salt.

Preparation of some of the intermediates of the compounds of this invention and the compounds of this invention are illustrated by the following examples. In the examples which follow, all percentages are given on a weight basis unless otherwise indicated.

EXAMPLE 1

This example describes the preparation of 6-[3-(trifluoromethyl)phenyl]-4-pyridazinecarboxylic acid ethyl ester (Compound No. 1) and 6-[3-(trifluoromethyl)phenyl]-4-pyridazinecarboxylic acid (Compound No. 2), which are useful as intermediates in Process II and are specific embodiments of Process I.

A. m-Trifluoromethylacetophenone (74 g, 0.394 mole), ethyl carbazate (43 g, 0.413 mole), and catalytic p-toluenesulfonic acid (20 mg) were refluxed under $N_2$ over a Dean-Stark trap in toluene (1.2 L) until the theoretical amount of water of reaction was removed (7.1 mL, 6 h). The solvent was then removed in vacuo and 2-(1-(3-(trifluoromethyl)phenyl)ethylidene)hydrazinecarboxylic acid ethyl ester (107 g, 100% yield) was obtained as a white solid which was recrystallized from cyclohexane, mp=94°–96° C.

Anal. Calc. for $C_{12}H_{13}N_2O_2F_3$: C, 52.56; H, 4.78; N, 10.21 Found: C, 52.62; H, 4.78; N, 10.23

B. 2-(1-(3-(Trifluoromethyl)phenyl)ethylidene)hydrazinecarboxylic acid ethyl ester (107 g, 0.394 mole), N-chlorosuccinimide (115.6 g, 0.866 mole), and catalytic benzoyl peroxide (10 mg) were slowly heated under $N_2$ to 55° C. in carbon tetrachloride (1.5 L) at which point the reaction mixture became exothermic. The exotherm was controlled with an ice bath to just below the boiling point of carbon tetrachloride. After the exotherm had subsided (15 min.), the mixture was refluxed for 2 h. The mixture was cooled and filtered to remove the succinimide. The solvent was removed in vacuo to give [2,2-dichloro-1-[3-(trifluoromethyl)phenyl]ethylidene]hydrazinecarboxylic acid ethyl ester as a gold colored oil which can be recrystallized from cyclohexane to give a white solid (132 g, 98% yield), mp=81°–83° C.

Anal. Calc. for $C_{12}H_{11}N_2O_2Cl_2F_3$: C, 42.00; H, 3.23; N, 8.16 Found: C, 42.03; H, 3.24; N, 8.12

C. Ethyl propiolate (3.43 g, 0.035 mole) was stirred under $N_2$ in methylene chloride (300 mL) at RT while morpholine (3.05 g, 0.035 mole) was added dropwise over 15 min. The mixture was then refluxed for 30 min. and then cooled to room temperature (RT). Diisopropylethylamine (5.65 g, 0.0437 mole) was then added to the mixture followed by the addition of [2,2-dichloro-1-[3-(trifluoromethyl)phenyl]ethylidene]hydrazinecarboxylic acid ethyl ester (10 g, 0.029 mole) which was added dropwise as a solution in methylene chloride (60 mL) over 30 min. The mixture was then refluxed for 18 h, cooled, and partitioned 2 times with water. The organic layer was dried ($MgSO_4$), filtered and evaporated in vacuo to give a crude solid. This solid was recrystallized from cyclohexane/ethyl acetate to give 6-(4-morpholinyl)-3-[3-(trifluoromethyl)phenyl]-1,5(6H)-pyridazindicarboxylic acid diethyl ester (7.26 g, 55% yield) as a yellow solid, mp=128°–129° C.

Anal. Calc. for $C_{21}H_{24}N_3O_5F_3$: C, 55.38; H, 5.31; N, 9.23 Found: C, 55.26; H, 5.35; N, 9.21

D. 6-(4-morpholinyl)-3-[3-(trifluoromethyl)phenyl]-1,5(6H)-pyridazindicarboxylic acid, diethyl ester (10.73 g, 0.024 mole) was refluxed in DMF (150 mL) for 30 min. The mixture was poured into water and extracted 3×100 mL with ethyl acetate. The organic layer was dried ($MgSO_4$), filtered through silica gel, and evaporated in vacuo to give a crude solid which was recrystallized from cyclohexane/ethyl acetate to give 6-[3-(trifluoromethyl)phenyl]-4-pyridazinecarboxylic acid ethyl ester (3.34 g, 47% yield, Compound No. 1) as a brown solid.

E. Ethyl propiolate (130 mL, 1.28 mole) was stirred under $N_2$ in methylene chloride (2.5 L) at RT while morpholine (112 mL, 1.28 mole) was added dropwise over 20 min. External cooling by means of an ice bath was employed. The mixture was then refluxed for 30 min. and then cooled to RT. Diisopropylethylamine (426.4 mL, 2.45 mole) was then added to the mixture followed by [2,2-dichloro-1-[3-(trifluoromethyl)phenyl]ethylidene]hydrazinecarboxylic acid ethyl ester (400 g, 1.17 mole) which was added dropwise as a solution in methylene chloride (800 mL) over 30 min. The mixture was then refluxed for 18 h, cooled, and partitioned 2 times with water. The organic layer was dried ($MgSO_4$), filtered and evaporated in vacuo to give a crude oil. The crude oil was taken up in 3 L of ethanol and then KOH 302 g of 86.6%, 4.66 moles) was added while the solution was stirred. The mixture was then refluxed under $N_2$ for 2 h. Water (500 mL) was then added and most of the ethanol was removed in vacuo. The mixture was then dissolved in 3 L of water and extracted 3×800 mL with methylene chloride which was discarded. The aqueous layer was then made acidic with 12N HCl to precipitate the pyridazine acid (gas is evolved). The acid is then dried in vacuo to give 6-[3-(trifluoromethyl)phenyl]-4-pyridazinecarboxylic acid (247 g, 79% yield, Compound No. 2) as a brown solid which was recrystallized from ethyl acetate/methanol.

EXAMPLE 2

This example illustrates the preparation of [6-[3-(trifluoromethyl)phenyl]-4-pyridazinyl]carbamic acid, 1,1-dimethylethyl ester (Compound No. 3) and 6-[3-(trifluoromethyl)phenyl]-4-pyridazinamine (Compound No. 4) which are specific embodiments reesulting from the practice of Process II.

A. 6-[3-(trifluoromethyl)phenyl]-4-pyridazinecarboxylic acid (30 g, 0.112 mole, Compound No. 2), diphenylphosphorylazide (33.9 g, 0.123 mole) and triethylamine (17 g, 0.168 mole) were refluxed under $N_2$ in t-butanol (250 mL) for 4 h. The mixture was then partitioned between ethyl acetate and water. The organic layer was dried ($MgSO_4$), filtered through silica gel and evaporated in vacuo to give a crude solid which can be utilized as is in the next step or chromatographed on a Prep-500 to give [6-[3-(trifluoromethyl)phenyl]-4-pyridazinyl]carbamic acid, 1,1-dimethylethyl ester (Compound No. 3) as a white solid which was recrystallized from cyclohexane/ethyl acetate.

B. The crude 6-[3-(trifluoromethyl)phenyl]-4-pyridazinyl]carbamic acid, 1,1-dimethylethyl ester (Compound No. 3) from the first described procedure was refluxed in 250 mL of 1:1, 1.2N HCl/ethanol for 2 h under $N_2$. The mixture was then poured in water and made basic with 2.5N NaOH. The aqueous layer was then extracted 3×200 mL with ethyl acetate. The organic layer was dried ($MgSO_4$), filtered, evaporated in vacuo to give a crude solid which was chromatographed on a Prep-500 using ethyl acetate to give 6-[3-(trifluoromethyl)phenyl]-4-pyridazinamine (8.2 g, 31% overall yield, Compound No. 4) as a brown solid which was recrystallized from cyclohexane/ethyl acetate.

EXAMPLE 3

This example illustrates the preparation of 5-chloro-3-[3-(trifluoromethyl)phenyl]pyridazine (Compound No. 5) and is a specific embodiment of the practice of Process II.

6-[3-(Trifluoromethyl)phenyl]-4-pyridazinamine (2.0 g, 0.0084 mole), t-butylnitrite (1.65 mL of 90%, 0.0125 mole), and $CuCl_2$ (1.69 g, 0.125 mole) were refluxed under $N_2$ in acetonitrile (100 mL) for 4 h. The solution was then evaporated to dryness and triturated with ethyl acetate/cyclohexane 1:1. The solution was then passed through a plug of silica gel and evaporated in vacuo to give a crude solid which was recrystallized from cyclohexane/ethyl acetate to give 5-chloro-3-[3-(trifluoromethyl)phenyl]pyridazine (0.72 g, 33% yield, Compound No. 5) as a white solid.

EXAMPLE 4

This example illustrates the preparation of 5-methoxy-3-[3-(trifluoromethyl)phenyl]pyridazine (Compound No. 8) and is a specific embodiment of the practice of Process II.

5-Chloro-3-[3-(trifluoromethyl)phenyl]pyridazine (4 g, 0.015 mole, Compound No. 5) and NaOMe in MeOH (16.71 g of a 25% by weight solution, 0.077 mole) were stirred at RT under $N_2$ in MeOH (100 mL) for 4 h. The mixture was then partitioned between ethyl acetate and water. The organic layer was dried ($MgSO_4$), filtered and evaporated in vacuo. The crude solid was recrystallized from ethyl acetate/cyclohexane to give 5-methoxy-3-[3-(trifluoromethyl)phenyl]pyridazine (2.92 g, 74% yield, Compound No. 8) as a brown solid.

EXAMPLE 5

This example illustrates the preparation of 6-[3-(trifluoromethyl)phenyl]-4-pyridazinol (Compound No. 25) and is a specific embodiment of the practice of Process II.

5-Chloro-3-[3-(trifluoromethyl)phenyl]pyridazine (2 g, 0.0077 mole, Compound No. 5), 2.5N NaOH (50 mL) and DMSO (100 mL) were refluxed under $N_2$ for 2 h. The mixture was then allowed to cool and made acidic with 12N HCl and extracted 3×100 mL with ethyl acetate. The organic layer was dried ($MgSO_4$), filtered and evaporated in vacuo to give a crude solid which was recrystallized from methanol to give 6-[3-(trifluoromethyl)phenyl]-4-pyridazinol (1 g, 54% yield, Compound No. 25) as a light brown solid.

EXAMPLE 6

This example illustrates the preparation of 5-(difluoromethoxy)-3-[3-(trifluoromethyl)phenyl]pyridazine (Compound No. 49) and is a specific embodiment of the practice of Process II.

6-[3-(Trifluoromethyl)phenyl]-4-pyridazinol (2 g, 0.0083 mole, Compound No. 25), 50% NaOH (8 g, 0.1 mole) and DMF (100 mL) were stirred at RT while $CF_2ClH$ was continuously bubbled through the solution. After about 15 min. an exotherm began that was controlled with the use of an ice bath. The reaction was continued for 3 h. After this time the mixture was poured into water and extracted 3×100 mL with ethyl acetate. The organic layer was washed with water, dried ($MgSO_4$), filtered through silica gel and evaporated in vacuo. The residue was chromatographed on a Prep-500 to give 5-(difluoromethoxy)-3-[3-(trifluoromethyl)phenyl]pyridazine (0.63 g, 26% yield, Compound No. 49) as a brown solid which was recrystallized from cyclohexane, mp=70°–72° C.

EXAMPLE 7

This example illustrates the preparation of 5-chloro-6-[3-(trifluoromethyl)phenyl]-4-pyridazinamine (Compound No. 35) and is a specific embodiment of the practice of Process II.

6-[3-(Trifluoromethyl)phenyl]-4-pyridazinamine (2.0 g, 0.0084 mole, Compound No. 4) and N-chlorosuccinimide (0.61 g, 0.004 mole) were refluxed under $N_2$ in $CH_3CN$ (50 mL) for 1.5 h. After this time no starting material was present by TLC. The mixture was partitioned between EtOAc/water. The organic layer was extracted again with water, dried ($MgSO_4$), filtered and evaporated to give a crude oil. The oil was chromatographed on a Prep-500 using EtOAc/cyclohexane (9:1) to give a crude solid. The solid was recrystal-lized from EtOAc/cyclohexane to give 5-chloro-6-[3-(trifluoromethyl)phenyl]-4-pyridazinamine (0.57 g, 50% yield, Compound No. 35) as a tan solid.

EXAMPLE 8

This example illustrates the preparation of 4,5-dichloro-3-[3-(trifluoromethyl)phenyl]pyridazine (Compound No. 36) and 3,4,5-trichloro-3-[3-(trifluoromethyl)phenyl]pyridazine (Compound No. 38) and is a specific embodiment of the practice of Process II.

5-Chloro-6-[3-(trifluoromethyl)phenyl]-4-pyridazinamine (8.6 g, 0.036 moles, Compound No. 35) and N-chlorosuccinimide (5.1 g, 0.038 mole) were refluxed in acetonitrile (100 mL) for 1 h. After this time no apparent reaction had occurred. The mixture was cooled and then copper (II) chloride (5.4 g, 0.040 mole) was added, followed by t-butylnitrite (5.1 g, 0.044 mole) which was added dropwise as a solution in $CH_3CN$ (50 mL) over 10 min. The mixture was then refluxed for 1.5 h. After this time no starting material was present by TLC. The mixture was partitioned between 1.2N HCl/EtOAc. The organic layer was extracted again with 1.2N HCl, washed with brine, dried ($MgSO_4$), filtered and evaporated to give a crude oil. The oil was chromatographed on a Prep-500 using EtOAc/cyclohexane (1:9) to give two fractions.

The first fraction was recrystallized from pet. ether at low temperature to give 3,4,5-trichloro-3-[3-(trifluoromethyl)phenyl]pyridazine (0.2 g, 2% yield, Compound No. 38) as a tan solid.

The second fraction contained the 4,5-dichloro-3-[3-(trifluoromethyl)phenyl]pyridazine (4.78 g, 45% yield, Compound No. 36) as a yellow solid which can be recrystallized from cyclohexane.

EXAMPLE 9

This example illustrates the preparation of 4,5-difluoro-3-[3-(trifluoromethyl)phenyl]pyridazine (Compound No. 44) and is a specific embodiment of the practice of Process II.

4,5-Dichloro-3-[3-(trifluoromethyl)phenyl]pyridazine (8.56 g, 0.029 mole, Compound No. 36) and anhydrous KF (8.4 g, 0.145 moles) were heated to 120° C. in DMF (100 mL) under $N_2$ for 2.5 h. The mixture was then poured into water and extracted 3×100 mL with ethyl acetate. The combined organic layers were washed with brine, dried ($MgSO_4$), filtered through silica gel and evaporated in vacuo. The crude oil was purified by chromatography on a Prep-500 to give 4,5-difluoro-3-[3-(trifluoromethyl)phenyl]pyridazine (5.3 g, 70% yield, Compound No. 44) as a light yellow solid which was recrystallized from cyclohexane.

EXAMPLE 10

This example illustrates the preparation of 5-fluoro-4-methoxy-3-[3-(trifluoromethyl)phenyl]pyridazine (Compound No. 45) and 4-fluoro-5-methoxy-3-[3-(trifluoromethyl)phenyl]pyridazine (Compound No. 46) which are specific embodiments of the practice of Process II.

4,5-Difluoro-3-[3-(trifluoromethyl)phenyl]pyridazine (0.9 g, 0.0035 mole) and potassium hydroxide (0.2 g, 0.0035 mole) were stirred under $N_2$ at RT in MeOH (50 mL) for 20 min. After this time no starting material was present by TLC. The mixture was partitioned between EtOAc-water. The aqueous layer was extracted again with EtOAc. The EtOAc layers were combined, dried ($MgSO_4$), filtered and evaporated to give a crude oil. The oil was chromatographed on a Prep-500 using EtOAc-cyclohexane (2:3) to give two fractions.

The first fraction was identified as 5-fluoro-4-methoxy-3-[3-(trifluoromethyl)phenyl]pyridazine (0.32 g, 34% yield, Compound No. 45) and was obtained as an off-white solid.

The second fraction was identified as 4-fluoro-5-methoxy-3-[3-(trifluoromethyl)phenyl]pyridazine (0.5 g, 52% yield, Compound No. 46) and was obtained as an off-white solid.

EXAMPLE 11

This example illustrates the preparation of 5-methoxy-N-methyl-3-[3-(trifluoromethyl)phenyl]-4-pyridazinamine (Compound No. 86) and is a specific embodiment of the practice of Process II.

4-Fluoro-5-methoxy-3-[3-(trifluoromethyl)phenyl]pyridazine (0.6 g, 0.0022 mole, Compound No. 46) and methylamine (1.54 g of a 40% solution in water, 0.0194 mole) were stirred at RT in THF (20 mL) under $N_2$ for 24 h. The mixture was poured into water and extracted 3×50 mL with ethyl acetate. The organic layer was dried ($MgSO_4$), filtered, and evaporated in vacuo. The crude solid was recrystallized from cyclohexane/ethyl acetate to give 5-methoxy-N-methyl-3-[3-(trifluoromethyl)phenyl]-4-pyridazinamine (0.59 g, 95% yield, Compound No. 86) as an off white solid.

EXAMPLE 12

This example illustrates the preparation of 4-ethenyl-5-methoxy-3-[3-(trifluoromethyl)phenyl]pyridazine (Compound No. 55) and is a specific embodiment of the practice of Process II.

4-Bromo-5-methoxy-3-[3-(trifluoromethyl)phenyl]pyridazine (1.0 g, 0.003 mole, Compound No. 57), vinyltributyltin (1.1 g, 0.0034 mole) and trans-benzyl(chloro)bis-(triphenylphosphine)-palladium(II) (20 mg) were heated to 110° C. in DMF (50 mL) under $N_2$ for 4 h. The reaction was then cooled and partitioned between aqueous KF and ethyl acetate. The KF solution was extracted with additional ethyl acetate. The organic layers were washed with brine, dried ($MgSO_4$), filtered through silica gel and then evaporated in vacuo. The crude oil was then chromatographed on a Prep-500 to give 4-ethenyl-5-methoxy-3-[3-(trifluoromethyl)phenyl]pyridazine (0.35 g, 42% yield, Compound No. 55) as a light brown solid.

EXAMPLE 13

This example illustrates the preparation of 5-chloro-3-[3-(trifluoromethyl)phenyl]pyridazine, 1-oxide (Compound No. 70) and 3,4-dichloro-6-[3-(trifluoromethyl)phenyl]pyridazine (Compound No. 47) and is a specific embodiment of the practice of Process II.

5-Chloro-3-[3-(trifluoromethyl)phenyl]pyridazine (23.4 g, 0.09 mole, Compound No. 5) and m-chloroperbenzoic acid (23.3 g of 80%, 0.11 mole) were refluxed under N₂ in chloroform (300 mL) for 1.5 h. The mixture was then partitioned between ethyl acetate and saturated sodium bicarbonate solution. The aqueous layer was extracted again with ethyl acetate. The organic layers were then washed with brine, dried (MgSO₄), filtered and evaporated in vacuo. The 5-chloro-3-[3-(trifluoromethyl)phenyl]pyridazine, 1-oxide (28.5 g, 100% yield, Compound No. 70) was obtained as a white solid which was recrystallized from ethyl acetate/cyclohexane.

5-Chloro-3-[3-(trifluoromethyl)phenyl]pyridazine, 1-oxide (27 g, 0.098 mole, Compound No. 70) and POCl₃ (16.9 g, 0.11 mole) were heated to 105° C. in toluene (250 mL) under N₂ for 18 h. The solvent was then removed in vacuo and the mixture was partitioned between ethyl acetate and water. The organic layer was washed with brine, dried (MgSO₄), filtered through silica gel and evaporated in vacuo. The crude solid was recrystallized from cyclohexane/ethyl acetate to give 3,4-dichloro-6-[3-(trifluoromethyl)phenyl]pyridazine (21.57 g, 76% yield, Compound No. 47) as a white solid.

EXAMPLE 14

This example illustrates the preparation of 3,4-difluoro-6-[3-(trifluoromethyl)phenyl]pyridazine (Compound No. 62) and is a specific embodiment of the practice of Process II.

3,4-Dichloro-6-[3-(trifluoromethyl)phenyl]pyridazine (2.0 g, 0.0068 mole, Compound No. 47) and anhydrous KF (2 g, 0.034 mole) were heated to 145° C. in DMF (50 mL) under N₂ for 3 h. The reaction mixture was poured into water and extracted 3×100 mL with ethyl acetate. The organic layer was dried (MgSO₄), filtered and evaporated in vacuo to give a crude oil which was chromatographed on a Prep-500 to give 3,4-difluoro-6-[3-(trifluoromethyl)phenyl]pyridazine (1.26 g, 71% yield, Compound No. 62) as a white solid.

EXAMPLE 15

This example illustrates the preparation of 3-fluoro-4-methoxy-6-[3-(trifluoromethyl)phenyl]pyridazine (Compound No. 63) and 4-fluoro-3-methoxy-6-[3-(trifluoromethyl)phenyl]pyridazine (Compound No. 74) and is a specific embodiment of the practice of Process II.

3,4-Difluoro-6-[3-(trifluoromethyl)phenyl]pyridazine (10.6 g, 0.041 mole, Compound No. 62) and sodium methoxide (7.2 g, 0.33 mole, 25% by weight solution in methanol) were stirred overnight under N₂ at RT in MeOH (250 mL). The reaction was stopped when there was ~5% starting material remaining. The mixture was partitioned between EtOAc-water. The aqueous layer was extracted again with EtOAc. The EtOAc layers were combined, washed with brine, dried (MgSO₄), filtered and evaporated to give a crude solid. The solid was chromatographed on a Prep-500 using EtOAc-cyclohexane (1:3) to give two fractions.

The first fraction was identified as 3-fluoro-4-methoxy-6-[3-(trifluoromethyl)phenyl]pyridazine (8.26 g, 73% yield, Compound No. 63) and was obtained as an off-white solid.

The second fraction was dissolved under N₂ at RT in MeOH and sodium methoxide added until all the starting material was gone by HPLC. The mixture was worked up as above to give a crude oil. The oil was chromatographed on a Prep-500 using EtOAc-cyclohexane (1:19) and then recrystallized from EtOAc-cyclohexane to give 4-fluoro-3-methoxy-6-[3-(trifluoromethyl)phenyl]pyridazine (0.8 g, 7% yield, Compound No. 74) as a white solid.

EXAMPLE 16

This example illustrates the preparation of 4-methoxy-3-(methylthio)-6-[3-(trifluoromethyl)phenyl]pyridazine (Compound No. 64) and is a specific embodiment of the practice of Process II.

3-Chloro-4-methoxy-6-[3-(trifluoromethyl)phenyl]pyridazine (2.0 g, 0.0069 mole, Compound No. 48) and sodium thiomethoxide (0.5 g, 0.0069 mole) were refluxed overnight under N₂ in THF (50 mL). After this time no starting material was present by TLC. The mixture was partitioned between EtOAc-water. The aqueous layer was extracted again with EtOAc. The EtOAc layers were combined, washed with brine, dried (MgSO₄), filtered and evaporated to give a crude oil. The oil was chromatographed on a Prep-500 using EtOAc-cyclohexane (3:17) to give 4-methoxy-3-(methylthio)-6-[3-(trifluoromethyl)phenyl]pyridazine (1.83 g, 88% yield, Compound No. 64) as a white solid.

EXAMPLE 17

This example illustrates the preparation of 4-methoxy-3-methyl-6-[3-(trifluoromethyl)phenyl]pyridazine (Compound No. 66) which is a specific embodiment of Process II.

3-Bromo-4-methoxy-6-[3-(trifluoromethyl)phenyl]pyridazine (1.0 g, 0.003 mole, Compound No. 65), tetramethyltin (1.28 g, 0.0072 mole) and trans-benzyl(chloro)bis-(triphenylphosphine)palladium(II) (20 mg) were heated to 100° C. in DMF under N₂ for 18 h. The reaction was then cooled and partitioned between aqueous KF solution and ethyl acetate. The KF solution was extracted with additional ethyl acetate. The organic layers were washed with brine, dried (MgSO₄), filtered through silica gel and then evaporated in vacuo. The crude oil was then chromatographed on a Prep-500 to give 4-methoxy-3-methyl-6-[3-(trifluoromethyl)phenyl]pyridazine (0.51 g, 63% yield, Compound No. 66) as a light yellow solid.

EXAMPLE 18

This example illustrates the preparation of 3-chloro-5-methoxypyridazine which is used as an intermediate in Process V and is a specific embodiment of the practice of Process III.

A. 4,5-Dichloro-3-hydroxypyridazine (3000 g, 18.18 moles), dihydropyran (1943 g, 23.08 mole), p-toluenesulfonic acid monohydrate (283 g, 1.49 moles) and 16 L of tetrahydrofuran were added to a 50 L round bottomed flask equipped with a heating mantle, reflux condenser and a mechanical stirrer. The mixture was stirred at reflux for 29 h. Additional dihydropyran was added at 6 h (1328 g, 15.79 mol) and at 21 h (780 g, 9.25 moles). The reaction mixture was allowed to cool to room temperature overnight. The mixture was concentrated in vacuo to an oily residue. The residue was taken up in 16 L of ethyl acetate and washed with 2N NaOH (2×6 L). The organic solution was dried (MgSO₄) and concentrated in vacuo to give 4,5-dichloro-2-(tetrahydro-2H-pyran-2-yl)-3(2H)-pyridazinone which was a black oily solid which was used without further purification in the next step. The product was purified by filtration through silica gel with ethyl acetate followed by evaporation and recrystallization from ethyl acetate/cyclohexane to give a white solid, mp=74°–76° C.

Anal. Calc. for $C_9H_{10}N_2O_2Cl_2$–0.1 $C_6H_{12}$: C, 44.78;H, 4.38;N, 10.89 Found: C, 44.63;H, 4.22;N, 10.94

B. 4,5-Dichloro-2-(tetrahydro-2H-pyran-2-yl)-3(2H)-pyridazinone from the previous step and 17 L of methanol were added to a 50 L round bottomed flask equipped with a glycol cooling jacket and a mechanical stirrer. The resulting solution was cooled to 0° C. and 87% KOH (1172 g 18.17 moles) was added in small portions over approximately 1 h. The mixture exothermed to 40° C. Following the addition, the mixture was stirred an additional 3 h. at ambient temperature. The reaction mixture was partitioned with 12 L of ethyl acetate and 12 L of $H_2O$. The aqueous layer was extracted with ethyl acetate (2×4 L). The combined organic layers were washed with brine (2×10 L) and dried ($MgSO_4$). The organic solution was clarified by filtration and concentrated to give a dark semi-solid. The crude material was added equally to two 22 L flasks. The material was suspended in 12 L hexanes/ethyl ether (2:1 ratio). The washed material was vacuum filtered on a Buchner funnel and air dried overnight to give 3,406 g (77% over 2 steps) of 4-chloro-5-methoxy-2-(tetrahydro-2H-pyran-2-yl)-3(2H)-pyridazinone as a dark tan solid suitable for further transformations. The product was purified by recrystallization from ethyl acetate/cyclohexane to give a white solid, mp=118°–120° C.

Anal. Calc. for $C_{10}H_{13}N_2O_3Cl$: C, 49.09; H, 5.36; N, 11.45 Found: C,49.04; H, 5.38; N, 11.43

C. 4-Chloro-5-methoxy-2-(tetrahydro-2H-pyran-2-yl)-3(2H)-pyridazinone (2486 g, 10.16 moles), ethanol (8 L), triethylamine (2 L, 14.23 moles) and 5% Pd-C (100 g of 50% water-wet Pd-C) were added to a 5 gallon (18.9L) autoclave. The mixture was hydrogenated at 50–60 psi (344–413 kilo Pascals) of $H_2$ and heated to a maximum temperature of 43° C. After 24 h., the reaction was complete. The reaction mixture was diluted with a small amount of water and vacuum filtered through celite. The filtrate was concentrated and partitioned with 10 L of ethyl acetate and 8 L of $H_2O$. The aqueous phase was extracted with ethyl acetate (2×2 L). The combined organics were washed with 5 L brine, dried ($MgSO_4$) and vacuum filtered. The solution was concentrated in vacuo to give 2133 g (100% yield) of 5-methoxy-2-(tetrahydro-2H-pyran-2-yl)-3(2H)-pyridazinone as a dark oil which later crystallized to give a tan product suitable for further transformations. The product was purified by recrystallization from ethyl acetate/cyclohexane to give a white solid, mp=76°–78° C.

Anal. Calc. for $C_{10}H_{14}N_2O_3$: C, 57.13; H, 6.71; N, 13.32 Found: C, 56.86; H, 6.61; N, 13.21

D. 5-Methoxy-2-(tetrahydro-2H-pyran-2-yl)-3(2H)-pyridazinone (2035 g, 9.69 moles) and 2 L of methanol were added to a 22 L round bottomed flask equipped with a heating mantle, reflux condenser and mechanical stirrer. The mixture was warmed to 35° C. and 8 L of 6N HCl was added and then the mixture was heated to reflux for 2 h. The reaction mixture was then cooled slightly and transferred to a glycol cooled 22 L flask where the mixture was cooled further to 30° C. The mixture was made basic (pH 13–14) by cautious addition of 50% NaOH in small portions. The basic mixture was extracted with $CH_2Cl_2$ (4×3 L). The aqueous phase was then acidified with concentrated HCl (pH 1–2) to precipitate the product. The product was collected by vacuum filtration on a Buchner funnel. The product was dried to constant weight on a fluid bed dryer at 70° C. This afforded 798 g (65% yield) of 3-hydroxy-5-methoxypyridazine as a white solid which was recrystallized from methanol, mp=253°–255° C.

Anal. Calc. for $C_5H_6N_2O_2$: C, 47.62; H, 4.80; N, 22.21 Found: C, 47.60; H, 4.83; N, 22.18

E. 3-Hydroxy-5-methoxypyridazine (629.6 g, 4.99 moles) and phosphorous oxychloride (2.5 L, 27 moles) were added to a 5 L round bottomed flask equipped with a heating mantle and a mechanical stirrer. The resulting stirred slurry was rapidly heated (<30 min) to 75° C. At this temperature the heating mantle was removed. The reaction mixture continued to exotherm to a final temperature of 82.3° C. After the solids had dissolved in the darkening reaction mixture, stirring was continued an additional 2 minutes. The homogeneous reaction mixture was then rapidly cooled to room temperature with an ice/water bath. The reaction mixture was concentrated via rotary evaporator using pump vacuum and a water bath temperature of 45° C. The residue was taken up in 2 L of $CH_2Cl_2$ and slowly poured into a stirring mixture of 2 L $CH_2Cl_2$ and 6 L of $H_2O$ chilled to 10° C. The layers were separated and enough 50% NaOH was added to the aqueous phase to give a pH of 2–4. The aqueous phase was extracted with additional $CH_2Cl_2$ (2×2 L). The combined organic layers were washed with 4 L of $H_2O$ and dried ($MgSO_4$). The solution was vacuum filtered through 1 kg of silica gel. The silica gel was washed with 4 L of ethyl acetate/hexanes (1:1). The filtrate was concentrated in vacuo to afford 564 g (78% yield) of 3-chloro-5-methoxypyridazine as a pale yellow solid. The product was stored in a freezer to prevent gradual decomposition. The product was recrystallized from ethyl acetate/cyclohexane to give a white solid, mp=98°–100° C.

Anal. Calc. for $C_5H_5N_2OCl$: C, 4.154; H, 3.49; N, 19.38 Found: C, 41.62; H, 3.51; N, 19.34

EXAMPLE 19

This example describes the preparation of 3-chloro-5-(methylthio)pyridazine which is useful as an intermediate in Process V and is a specific embodiment of Process IV.

2,4-Dichloropyridazine, which is a known compound, (2.0 g, 0.0135 moles) and sodium thiomethoxide (1.14 g, 0.0162 moles) were stirred in THF (50 mL) at RT under $N_2$ for 2 h. The mixture was then poured into water and extracted 2×100 mL with ethyl acetate. The organic layer was dried ($MgSO_4$), filtered and evaporated in vacuo to give a crude solid which was recrystallized from cyclohexane/ ethyl acetate to give 3-chloro-5-(methylthio)pyridazine (1.64 g, 76% yield) as a brown solid, mp=98°–100° C.

Anal. Calc. for $C_5H_5N_2ClS$: C, 37.39; H, 3.14; N, 17.44 Found: C, 37.47; H, 3.14; N, 17.49

Several other compounds of the present invention were prepared using generally the procedures illustrated above or other procedure obvious to one skilled in the art. Specific compounds illustrated of the present invention are given below where the prepared compounds are structurally depicted and named. Melting points and elemental analyses are provided for these compounds in the following table.

| Cmp No. | Name | Structure | Analysis (%) Calc'd Found |
|---|---|---|---|
| 1 | 4-PYRIDAZINECARBOXYLIC ACID, 6-[3-(TRIFLUOROMETHYL)PHENYL]-ETHYL ESTER<br>MP: 131.0–132.0 | 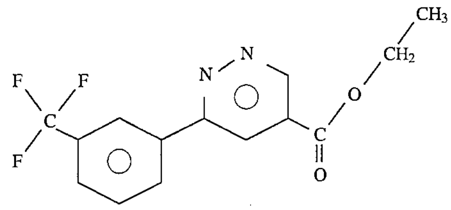 | C 56.76 56.82<br>H 3.74 3.77<br>F 19.24<br>N 9.46 9.41 |
| 2 | 4-PYRIDAZINECARBOXYLIC ACID, 6-[3-(TRIFLUOROMETHYL)PHENYL]-<br>MP: 200.0–202.0 | 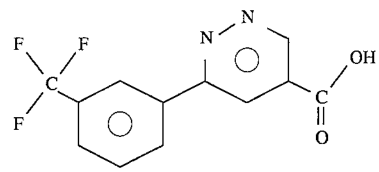 | C 53.74 53.49<br>H 2.63 2.69<br>F 21.25<br>N 10.45 10.31 |
| 3 | CARBAMIC ACID, [6-[3-(TRIFLUOROMETHYL)PHENYL]-4-PYRIDAZINYL]-, 1,1-DIMETHYLETHYL ESTER<br>MP: 124.0–126.0 | 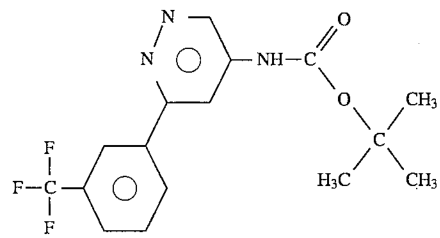 | C 56.63 56.67<br>H 4.75 4.76<br>F 16.80<br>N 12.38 12.33 |
| 4 | 4-PYRIDAZINAMINE, 6-[3-(TRIFLUOROMETHYL)PHENYL]-<br>MP: 81.0–82.0 | 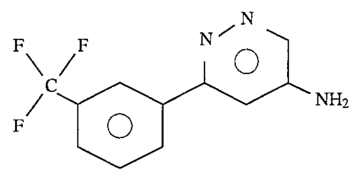 | C 55.23 54.49<br>H 3.37 3.46<br>F 23.83<br>N 17.57 17.35 |
| 5 | PYRIDAZINE, 5-CHLORO-3-[3-(TRIFLUOROMETHYL)PHENYL]-<br>MP: 117.0–118.0 | 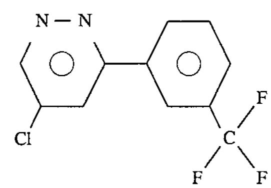 | C 51.08 50.23<br>H 2.34 2.29<br>Cl 13.71<br>F 22.04<br>N 10.83 10.65 |
| 6 | FORMAMIDE, N-[6-[(3-TRIFLUOROMETHYL)PHENYL]-4-PYRIDAZINYL]-<br>MP: 127.0–128.0 | 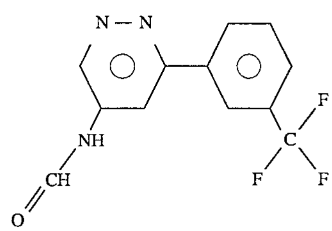 | C 53.94 53.92<br>H 3.02 3.04<br>F 21.33<br>N 15.73 15.70 |
| 7 | 4-PYRIDAZINAMINE, N-METHYL-6-[(3-TRIFLUOROMETHYL)PHENYL]-<br>MP: 162.0–164.0 | 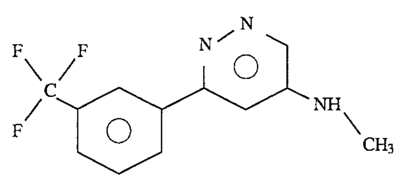 | C 56.92 56.85<br>H 3.98 3.98<br>F 22.51<br>N 16.59 16.54 |
| 8 | PYRIDAZINE, 5-METHOXY-3-[3-(TRIFLUOROMETHYL)PHENYL]-<br>MP: 100.0–102.0 | 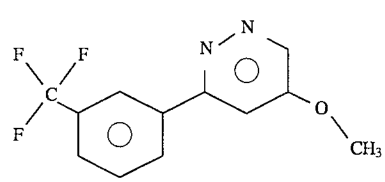 | C 56.70 55.75<br>H 3.57 3.49<br>F 22.42<br>N 11.02 10.79 |

| Cmp No. | Name | Structure | Analysis (%) Calc'd Found |
|---|---|---|---|
| 9 | 4-PYRIDAZINAMINE, N,N-DIMETHYL-6-[3-(TRIFLUOROMETHYL)PHENYL]- MP: 157.0–159.0 | 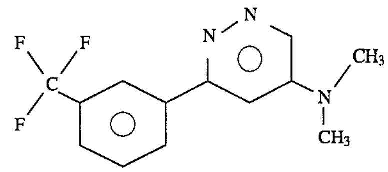 | C 58.42 57.49<br>H 4.53 4.65<br>F 21.33<br>N 15.72 15.44 |
| 10 | PYRIDAZINE, 5-BROMO-3-[3-(TRIFLUOROMETHYL)PHENYL]- MP: 220.0–222.0 | 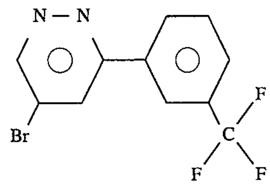 | C 43.59 43.47<br>H 2.00 1.96<br>Br 26.36<br>F 18.81<br>N 9.24 9.18 |
| 11 | PYRIDAZINE, 5-IODO-3-[3-(TRIFLUOROMETHYL)PHENYL]- MP: 124.0–125.0 | 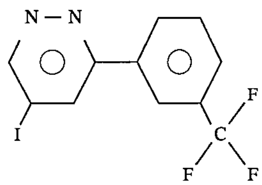 | C 37.74 37.58<br>H 1.73 1.75<br>F 16.28<br>I 36.25<br>N 8.00 7.96 |
| 12 | PYRIDAZINE, 5-ETHOXY-3-[3-(TRIFLUOROMETHYL)PHENYL]- MP: 105.0–106.0 | 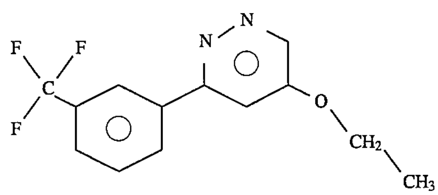 | C 58.21 57.65<br>H 4.13 4.08<br>F 21.25<br>N 10.44 10.34 |
| 13 | PYRIDAZINE, 5-PROPOXY-3-[3-(TRIFLUOROMETHYL)PHENYL]- MP: 101.0–102.0 | 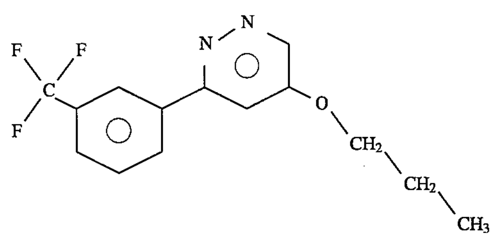 | C 59.57 59.37<br>H 4.64 4.63<br>F 20.19<br>N 9.92 9.90 |
| 14 | PYRIDAZINE, 5-(METHYLTHIO)-3-[3-(TRIFLUOROMETHYL)PHENYL]- MP: 109.0–110.0 | 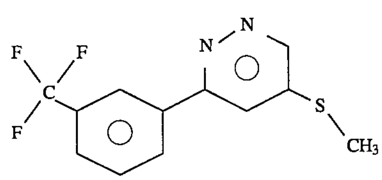 | C 53.33 52.36<br>H 3.36 3.44<br>F 21.09<br>N 10.36 10.15<br>S 11.86 |
| 15 | PYRIDAZINE, 5-(2-PROPYNYLOXY)-3-[3-(TRIFLUOROMETHYL)PHENYL]- MP: 76.0–78.0 | 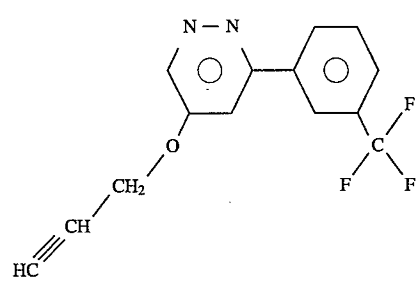 | C 60.44 59.62<br>H 3.26 3.34<br>F 20.49<br>N 10.07 9.92 |

-continued

| Cmp No. | Name | Structure | Analysis (%) Calc'd Found |
|---|---|---|---|
| 16 | PYRIDAZINE, 5-(2-PROPENYLOXY)-3-[3-(TRIFLUOROMETHYL)PHENYL]- MP: 83.0–84.0 | 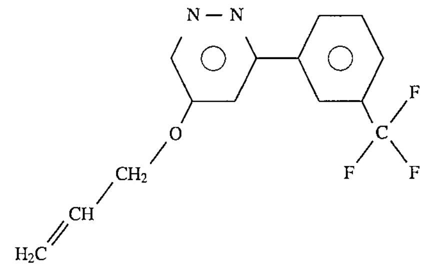 | C 60.00 59.92<br>H 3.96 4.00<br>F 20.34<br>N 10.00 9.92 |
| 17 | PYRIDAZINE, 5-(1-METHYLETHOXY)-3-[3-(TRIFLUOROMETHYL)PHENYL]- MP: 49.0–51.0 | 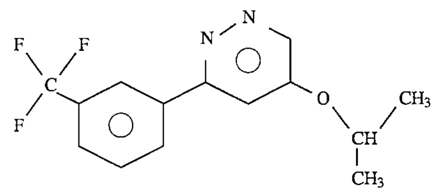 | C 59.57 59.49<br>H 4.64 4.65<br>F 20.19<br>N 9.92 9.86 |
| 18 | 4-PYRIDAZINOL, 6-[3-(TRIFLUOROMETHYL)PHENYL]-, SODIUM SALT MP: 280.0 | 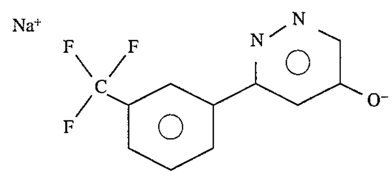 | C 50.39 42.08<br>H 2.31 3.34<br>F 21.74<br>N 10.69 8.67<br>Na 8.77 |
| 19 | PROPANOIC ACID, 2-[[6-[3-(TRIFLUOROMETHYL)PHENYL]-4-PYRIDAZINYL]OXY]-, ETHYL ESTER MP: 93.0–96.0 | 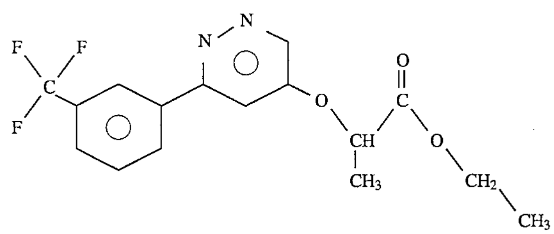 | C 56.47 54.14<br>H 4.44 4.52<br>F 16.75<br>N 8.23 7.81 |
| 20 | PYRIDAZINE, 5-[(2-METHOXYETHOXY)METHOXY]-3-[3-(TRIFLUOROMETHYL)PHENYL]- MP: 77.0–80.0 | 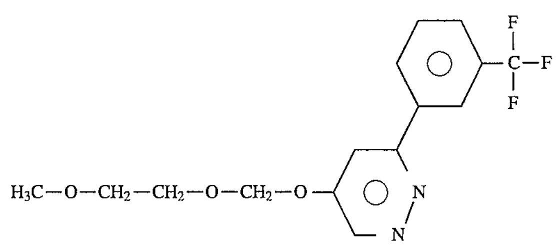 | C 54.88 53.61<br>H 4.61 4.81<br>F 17.36<br>N 8.53 8.26 |
| 21 | PYRIDAZINE, 5-(METHOXYMETHOXY)-3-[3-(TRIFLUOROMETHYL)PHENYL]- MP: 126.0–128.0 | 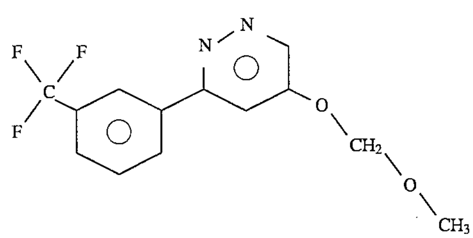 | C 54.93 55.03<br>H 3.90 3.89<br>F 20.05<br>N 9.86 9.79 |
| 22 | 4-PYRIDAZINECARBOXAMIDE, 6-[3-(TRIFLUOROMETHYL)PHENYL]- MP: 211.0–213.0 | 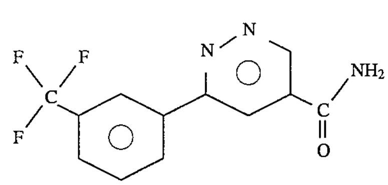 | C 53.94 54.01<br>H 3.02 3.06<br>F 21.33<br>N 15.73 15.72 |

-continued

| Cmp No. | Name | Structure | Analysis (%) Calc'd Found |
|---|---|---|---|
| 23 | PYRIDAZINE, 5-[(METHYLTHIO)METHOXY]-3-[3-(TRIFLUOROMETHYL)PHENYL]-<br>MP: 101.0–103.0 | 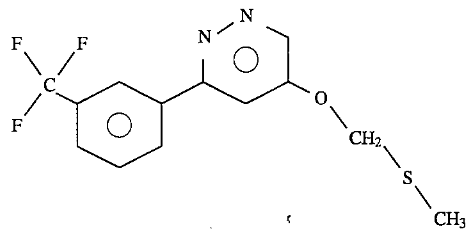 | C 51.99 50.55<br>H 3.69 3.93<br>F 18.98<br>N 9.33<br>S 10.68 |
| 24 | 4-PYRIDAZINAMINE, 6-[3,5-BIS(TRIFLUOROMETHYL)PHENYL]-<br>MP: 177.0–179.0 | 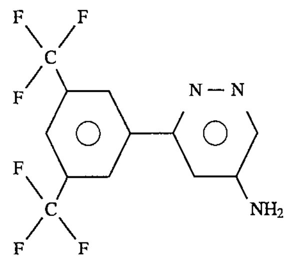 | C 46.92 46.41<br>H 2.30 2.49<br>F 37.11<br>N 13.68 13.53 |
| 25 | 4-PYRIDAZINOL, 6-[3-(TRIFLUOROMETHYL)PHENYL]-<br>MP: 270.0–271.0 | 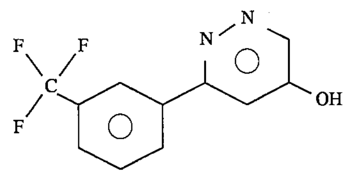 | C 55.01 54.45<br>H 2.94 3.01<br>F 23.73<br>N 11.66 11.50 |
| 26 | PYRIDAZINE, 5-METHOXY-3-[3-(TRIFLUOROMETHYL)PHENYL]-, MONOHYDROCHLORIDE<br>MP: 135.0–136.0 | * HCl | C 49.58 49.43<br>H 3.47 3.50<br>Cl 12.20<br>F 19.61<br>N 9.64 9.54 |
| 27 | PYRIDAZINIUM, 1-HYDROYX-4-METHOXY-6-[3-(TRIFLUOROMETHYL)PHENYL]-, N-OXIDE<br>MP: 145.0–147.0 | One structure OR the other | C 53.34 52.32<br>H 3.36 3.27<br>F 21.09<br>N 10.37 10.11 |
| 28 | METHANAMINE, N-METHYL-N-[[6-[3-(TRIFLUOROMETHYL)PHENYL]-4-PYRIDAZINYL]OXY]-<br>MP: 65.0–66.0 | 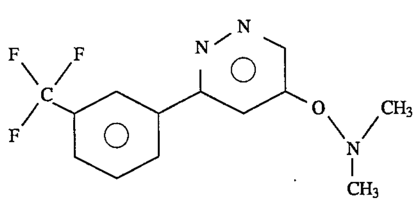 | C 55.12 55.11<br>H 4.27 4.27<br>F 20.12<br>N 14.83 14.79 |

-continued

| Cmp No. | Name | Structure | Analysis (%) Calc'd Found |
|---|---|---|---|
| 29 | PYRIDAZINE, 5-METHOXY-3-[3-(TRIFLUOROMETHYL) PHENYL]-, METHANESULFONATE MP: 137.0–139.0 | 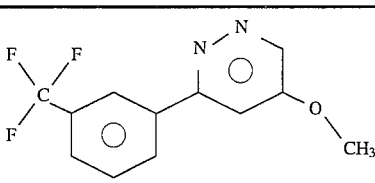 | C 44.57 44.34<br>H 3.74 3.80<br>F 16.27<br>N 8.00 7.94<br>S 9.15 |
| 30 | ACETIC ACID, TRIFLUORO-, COMPD. WITH 5-METHOXY-3-[3-(TRIFLUOROMETHYL) PHENYL)PYRIDAZINE (1:1) MP: 85.0–86.0 | 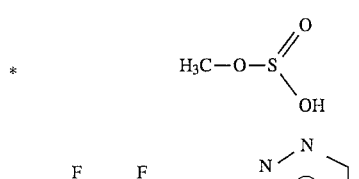 | C 45.66 45.63<br>H 2.74 2.75<br>F 30.96<br>N 7.61 7.59 |
| 31 | PYRIDAZINE, 5-METHOXY-3-[3-NITRO-5-(TRIFLUOROMETHYL)PHENYL]- MP: 105.0–107.0 | 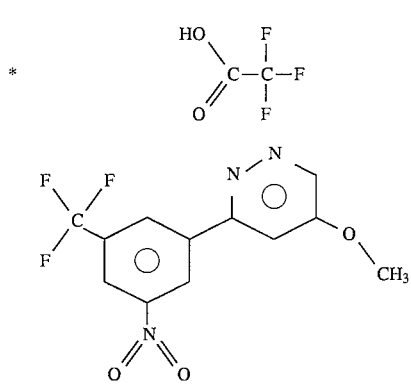 | C 48.17 48.26<br>H 2.70 2.75<br>F 19.05<br>N 14.04 13.97 |
| 32 | PYRIDAZINE, 5-METHOXY-3-[4-NITRO-3-(TRIFLUOROMETHYL)PHENYL]- MP: 95.0–96.0 | 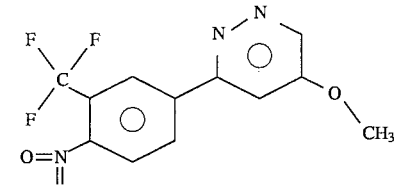 | C 48.17 48.33<br>H 2.70 2.78<br>F 19.05<br>N 14.04 14.11 |
| 33 | 4-PYRIDAZINAMINE, 5-BROMO-6-[3-(TRIFLUOROMETHYL)PHENYL]- MP: 189.0–192.0 | 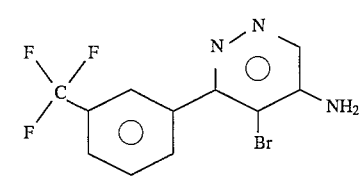 | C 41.53 41.61<br>H 2.22 2.25<br>Br 25.12<br>F 17.92<br>N 13.21 13.17 |
| 34 | 4-PYRIDAZINAMINE, 3,5-DIBROMO-6-[3-(TRIFLUOROMETHYL)PHENYL]- MP: 176.0–178.0 | 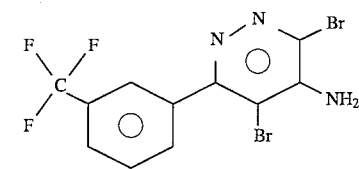 | C 33.28 33.14<br>H 1.52 1.54<br>Br 40.26<br>F 14.36<br>N 10.58 10.51 |
| 35 | 4-PYRIDAZINAMINE, 5-CHLORO-6-[3-(TRIFLUOROMETHYL)PHENYL]- MP: 186.0–188.0 | 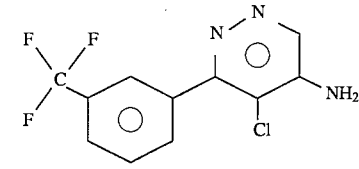 | C 48.28 48.27<br>H 2.58 2.62<br>Cl 12.96<br>F 20.83<br>N 15.36 15.26 |

-continued

| Cmp No. | Name | Structure | Analysis (%) Calc'd Found |
|---|---|---|---|
| 36 | PYRIDAZINE, 4,5-DICHLORO-3-[3-(TRIFLUOROMETHYL)PHENYL]- MP: 50.0–52.0 | 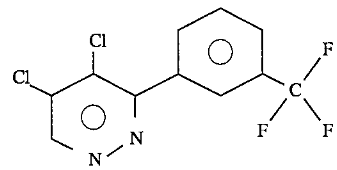 | C 45.08 45.15<br>H 1.72 1.74<br>Cl 24.19<br>F 19.45<br>N 9.56 9.52 |
| 37 | PYRIDAZINE, 5-CHLORO-4-METHOXY-3-[3-(TRIFLUOROMETHYL)PHENYL]- MP: 40.0–42.0 | 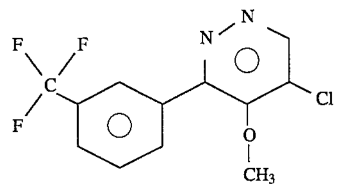 | C 49.93 50.08<br>H 2.79 2.84<br>Cl 12.28<br>F 19.75<br>N 9.70 9.65 |
| 38 | PYRIDAZINE, 3,4,5-TRICHLORO-3-[3-(TRIFLUOROMETHYL)PHENYL]- MP: 93.0–95.0 | 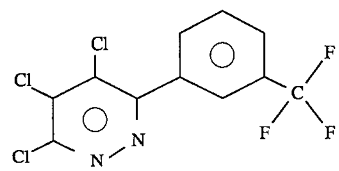 | C 40.34 40.44<br>H 1.23 1.26<br>Cl 32.47<br>F 17.40<br>N 8.55 8.61 |
| 39 | PYRIDAZINE, 4-CHLORO-5-METHOXY-3-[3-(TRIFLUOROMETHYL)PHENYL]- MP: 49.0–51.0 | 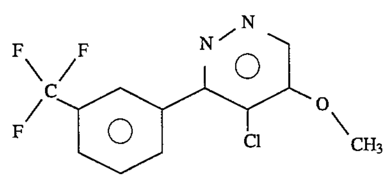 | C 49.93 50.12<br>H 2.79 2.82<br>Cl 12.28<br>F 19.75<br>N 9.70 9.76 |
| 40 | PYRIDAZINE, 4,5-DIMETHOXY-3-[3-(TRIFLUOROMETHYL)PHENYL]- MP: 75.0–77.0 | 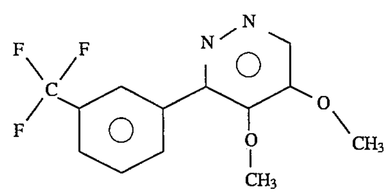 | C 54.93 54.85<br>H 3.90 3.95<br>F 20.05<br>N 9.86 9.83 |
| 41 | 4-PYRIDAZINAMINE, 5-BROMO-3-METHOXY-6-[3-(TRIFLUOROMETHYL)PHENYL]- MP: 182.0–184.0 | 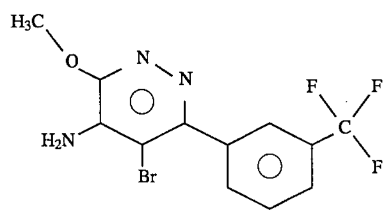 | C 41.40 41.50<br>H 2.61 2.64<br>Br 22.95<br>F 16.37<br>N 12.07 11.99 |
| 42 | PYRIDAZINE, 5-BROMO-4-METHOXY-3-[3-(TRIFLUOROMETHYL)PHENYL]- MP: | 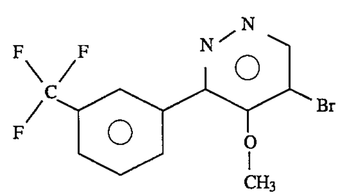 | C 43.27 43.32<br>H 2.42 2.46<br>Br 23.99<br>F 17.11<br>N 8.41 8.33 |
| 43 | ACETAMIDE, N-[5-HYDROXY-6-[3-(TRIFLUOROMETHYL)PHENYL]-4-PYRIDAZINYL]- MP: 249.0–251.0 | 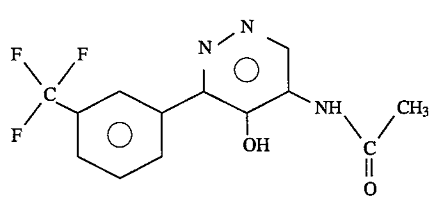 | C 52.53 51.40<br>H 3.39 3.33<br>F 19.18<br>N 14.14 13.76 |

-continued

| Cmp No. | Name | Structure | Analysis (%) Calc'd Found |
|---|---|---|---|
| 44 | PYRIDAZINE, 4,5-DIFLUORO-3-[3-(TRIFLUOROMETHYL)PHENYL]- MP: 88.0–90.0 | 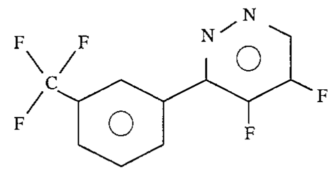 | C 50.78 50.83<br>H 1.94 1.94<br>F 36.51<br>N 10.77 10.68 |
| 45 | PYRIDAZINE, 5-FLUORO-4 METHOXY-3-[3-(TRIFLUOROMETHYL)PHENYL]- MP: 47.0–49.0 | 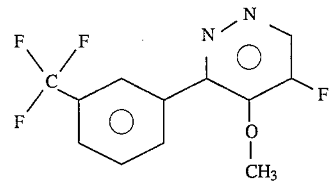 | C 52.95 53.03<br>H 2.96 2.97<br>F 27.92<br>N 10.29 10.32 |
| 46 | PYRIDAZINE, 4-FLUORO-5-METHOXY-3-[3-(TRIFLUOROMETHYL)PHENYL]- MP: 84.0–86.0 | 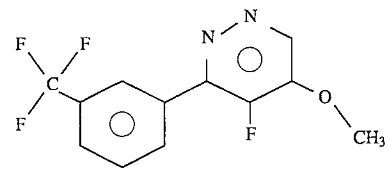 | C 52.95 53.03<br>H 2.96 3.00<br>F 27.92<br>N 10.29 10.20 |
| 47 | PYRIDAZINE, 3,4-DICHLORO-6-[3-(TRIFLUOROMETHYL)PHENYL]- MP: 114.0–116.0 | 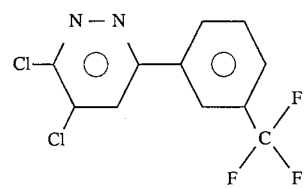 | C 45.08 45.15<br>H 1.72 1.72<br>Cl 24.19<br>F 19.45<br>N 9.56 9.53 |
| 48 | PYRIDAZINE, 3-CHLORO-4-METHOXY-6-[3-(TRIFLUOROMETHYL)PHENYL]- MP: 78.0–80.0 | 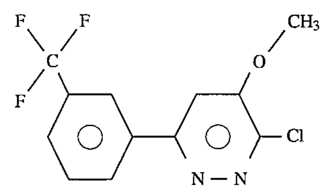 | C 49.93 48.72<br>H 2.79 2.70<br>Cl 12.28<br>F 19.75<br>N 9.70 9.39 |
| 49 | PYRIDAZINE, 5-(DIFLUOROMETHOXY)-3-[3-(TRIFLUOROMETHYL)PHENYL]- MP: 70.0–72.0 | 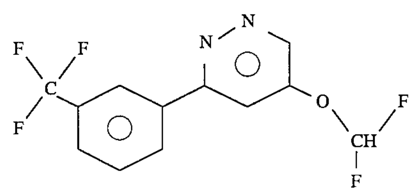 | C 49.67 49.61<br>H 2.43 2.44<br>F 32.74<br>N 9.65 9.61 |
| 50 | PYRIDAZINE, 3,4-DIMETHOXY-6-[3-(TRIFLUOROMETHYL)PHENYL]- MP: 87.0–89.0 | 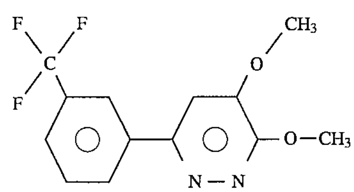 | C 54.93 54.83<br>H 3.90 3.90<br>F 20.05<br>N 9.86 9.90 |
| 51 | 4-PYRIDAZINECARBOXAMIDE, 6-[3,5-BIS(TRIFLUOROMETHYL)PHENYL]- MP: 228.0 | 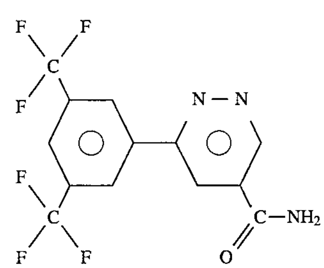 | C 46.58 45.96<br>H 2.10 2.23<br>F 34.01<br>N 12.54 12.31 |

| Cmp No. | Name | Structure | Analysis (%) Calc'd Found |
|---|---|---|---|
| 52 | BENZENAMINE, 3-(5-METHOXY-3-PYRIDAZINYL)-5-(TRIFLUOROMETHYL)- MP: 111.0–113.0 | 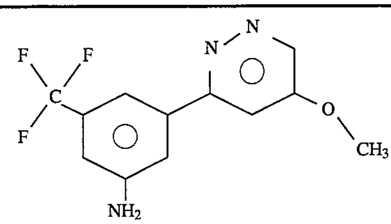 | C 53.53 53.41<br>H 3.74 3.75<br>F 21.17<br>N 15.61 15.53 |
| 53 | PYRIDAZINE, 3-[3-CHLORO-5-(TRIFLUOROMETHYL)PHENYL]-5-METHOXY- MP: 89.0–90.0 | 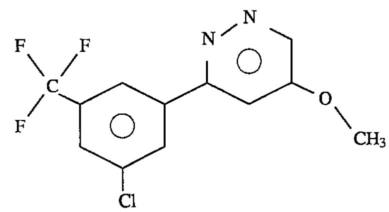 | C 49.93 50.00<br>H 2.79 2.81<br>Cl 12.28<br>F 19.75<br>N 9.70 9.68 |
| 54 | BENZENAMINE, 4-(5-METHOXY-3-PYRIDAZINYL)-2-(TRIFLUOROMETHYL)- MP: 185.0 | 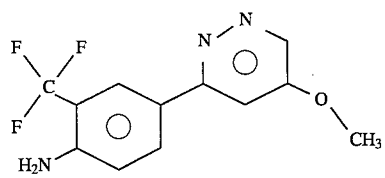 | C 53.53 52.33<br>H 3.74 3.65<br>F 21.17<br>N 15.61 15.10 |
| 55 | PYRIDAZINE, 4-ETHENYL-5-METHOXY-3-[3-(TRIFLUOROMETHYL)PHENYL]- MP: 66.0–68.0 | 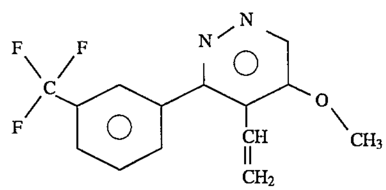 | C 60.00 59.88<br>H 3.96 3.97<br>F 20.34<br>N 10.00 9.91 |
| 56 | 4-PYRIDAZINAMINE, 5-CHLORO-N-METHYL-6-[3-(TRIFLUOROMETHYL)PHENYL]- MP: 169.0–171.0 | 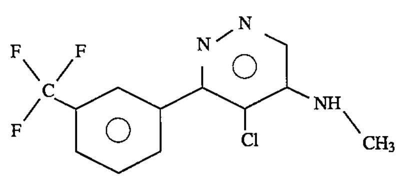 | C 50.10 50.09<br>H 3.15 3.16<br>Cl 12.32<br>F 19.81<br>N 14.61 14.62 |
| 57 | PYRIDAZINE, 4-BROMO-5-METHOXY-3-[3-(TRIFLUOROMETHYL)PHENYL]- MP: 53.0–55.0 | 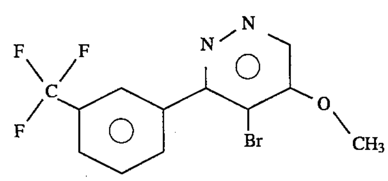 | C 43.27 43.36<br>H 2.42 2.41<br>Br 23.99<br>F 17.11<br>N 8.41 8.37 |
| 58 | PYRIDAZINE, 4,5-BIS(METHYLTHIO)-3-[3-(TRIFLUOROMETHYL)PHENYL]- MP: 120.0–122.0 | 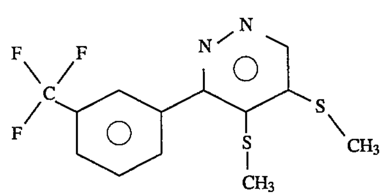 | C 49.35 49.41<br>H 3.50 3.53<br>F 18.02<br>N 8.85 8.83<br>S 20.27 |
| 59 | 4-PYRIDAZINAMINE, 5-FLUORO-N-METHYL-6-[3-(TRIFLUOROMETHYL)PHENYL]- MP: 180.0–182.0 | 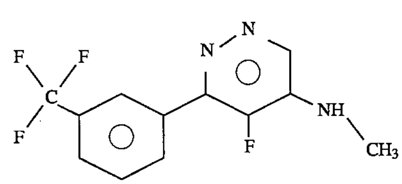 | C 53.14 53.28<br>H 3.34 3.36<br>F 28.02<br>N 15.49 15.55 |

| Cmp No. | Name | Structure | Analysis (%) Calc'd Found |
|---|---|---|---|
| 60 | PYRIDAZINE, 5-METHOXY-4-METHYL-3-[3-(TRIFLUOROMETHYL)PHENYL]- MP: 82.0–84.0 | 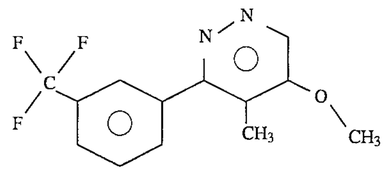 | C 58.21 58.28<br>H 4.13 4.15<br>F 21.25<br>N 10.44 10.40 |
| 61 | PYRIDAZINE, 4-ETHYL-5-METHOXY-3-[3-(TRIFLUOROMETHYL)PHENYL]- MP: 107.0–109.0 | 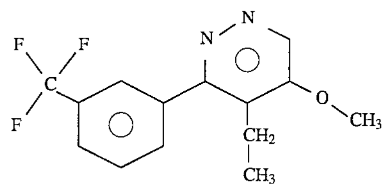 | C 59.57 59.48<br>H 4.64 4.68<br>F 20.19<br>N 9.92 9.88 |
| 62 | PYRIDAZINE, 3,4-DIFLUORO-6-[3-(TRIFLUOROMETHYL)PHENYL]- MP: 97.0–99.0 | 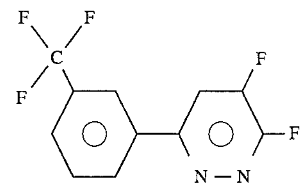 | C 50.78 50.76<br>H 1.94 1.89<br>F 36.51<br>N 10.77 10.72 |
| 63 | PYRIDAZINE, 3-FLUORO-4-METHOXY-6-[3-(TRIFLUOROMETHYL)PHENYL]- MP: 107.0–109.0 | 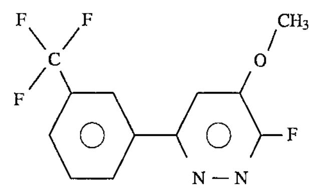 | C 52.95 52.96<br>H 2.96 2.97<br>F 27.92<br>N 10.29 10.21 |
| 64 | PYRIDAZINE, 4-METHOXY-3-(METHYLTHIO)-6-[3-(TRIFLUOROMETHYL)PHENYL]- MP: 108.0–110.0 | 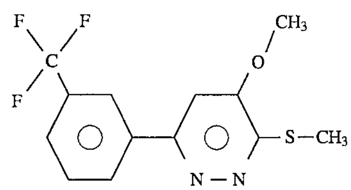 | C 51.99 52.07<br>H 3.69 3.69<br>F 18.98<br>N 9.33 9.38<br>S 10.68 |
| 65 | PYRIDAZINE, 3-BROMO-4-METHOXY-6-[3-(TRIFLUOROMETHYL)PHENYL]- MP: 83.0–85.0 | 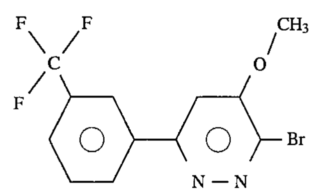 | C 43.27 43.35<br>H 2.42 2.41<br>Br 23.99<br>F 17.11<br>N 8.41 8.35 |
| 66 | PYRIDAZINE, 4-METHOXY-3-METHYL-6-[3-(TRIFLUOROMETHYL)PHENYL]- MP: 82.0–84.0 | 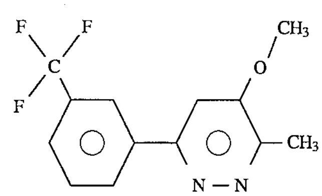 | C 58.21 58.10<br>H 4.13 4.13<br>F 21.25<br>N 10.44 10.42 |
| 67 | PYRIDAZINE, 3-ETHENYL-4-METHOXY-6-[3-(TRIFLUOROMETHYL)PHENYL]- MP: 105.0–107.0 | 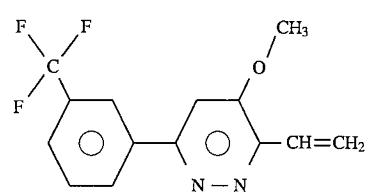 | C 60.00 60.10<br>H 3.96 3.98<br>F 20.34<br>N 10.00 10.05 |

-continued

| Cmp No. | Name | Structure | Analysis (%) Calc'd Found |
|---|---|---|---|
| 68 | PYRIDAZINE, 3-ETHYL-4-METHOXY-6-[3-(TRIFLUOROMETHYL)PHENYL]- MP: 91.0–94.0 | 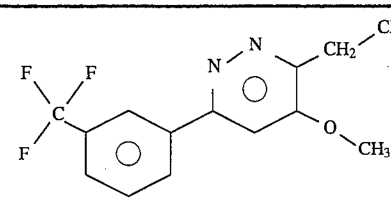 | C 59.57 59.63<br>H 4.64 4.64<br>F 20.19<br>N 9.92 9.85 |
| 69 | PYRIDAZINE, 3-[3-(TRIFLUOROMETHYL)PHENYL]-, 1-OXIDE MP: 92.0–94.0 | 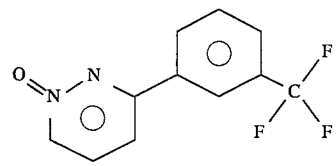 | C 55.01 54.85<br>H 2.94 2.89<br>F 23.73<br>N 11.66 11.53 |
| 70 | PYRIDAZINE, 5-CHLORO-3-[3-(TRIFLUOROMETHYL) PHENYL], 1-OXIDE MP: 147.0–149.0 | 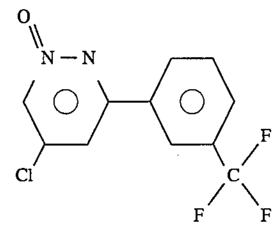 | C 48.11 48.03<br>H 2.20 2.18<br>Cl 12.91<br>F 20.75<br>N 10.20 10.12 |
| 71 | PYRIDAZINE, 3-CHLORO-6-[3-(TRIFLUOROMETHYL) PHENYL]- MP: 127.0–129.0 | 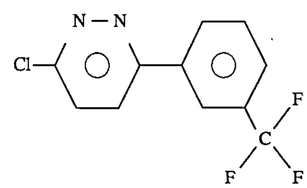 | C 51.08 51.00<br>H 2.34 2.29<br>Cl 13.71<br>F 22.04<br>N 10.83 10.82 |
| 72 | PYRIDAZINE, 5-FLUORO-3-[3-(TRIFLUOROMETHYL) PHENYL]- MP: 97.0–99.0 | 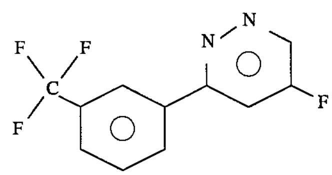 | C 54.55 54.46<br>H 2.50 2.49<br>F 31.38<br>N 11.57 11.51 |
| 73 | 3-PYRIDAZINAMINE, 4-METHOXY-N-METHYL-6-[3-(TRIFLUOROMETHYL)PHENYL]- MP: 89.0–91.0 | 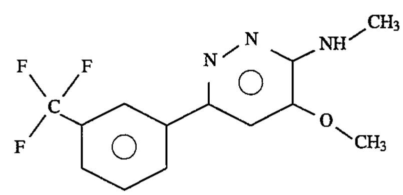 | C 55.12 55.06<br>H 4.27 4.30<br>F 20.12<br>N 14.83 14.78 |
| 74 | PYRIDAZINE, 4-FLUORO-3-METHOXY-6-[3-(TRIFLUOROMETHYL)PHENYL]- MP: 70.0–72.0 | 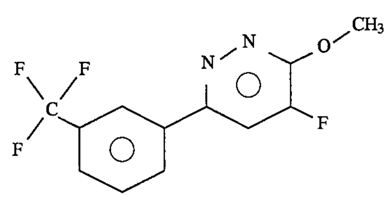 | C 52.95 53.60<br>H 2.96 3.03<br>F 27.92<br>N 10.29 10.23 |
| 75 | 3-PYRIDAZINOL, 4-METHOXY-6-[3-(TRIFLUOROMETHYL) PHENYL]- MP: 240.0 | 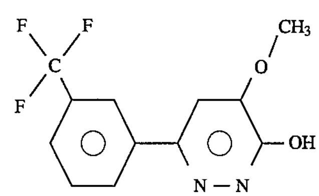 | C 53.34 53.36<br>H 3.36 3.37<br>F 21.09<br>N 10.37 10.33 |

-continued

| Cmp No. | Name | Structure | Analysis (%) Calc'd Found |
|---|---|---|---|
| 76 | PYRIDAZINE, 4-METHOXY-3-(METHYLSULFONYL)-6-[3-(TRIFLUOROMETHYL)PHENYL]- MP: 152.0–154.0 | 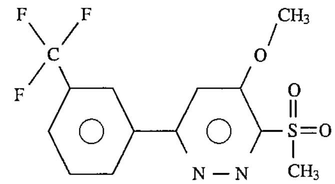 | C 46.99 47.09<br>H 3.34 3.37<br>F 17.15<br>N 8.43 8.43<br>S 9.65 |
| 77 | 3-PYRIDAZINECARBONITRILE, 4-METHOXY-6-[3-(TRIFLUOROMETHYL)PHENYL]- MP: 148.0–150.0 | 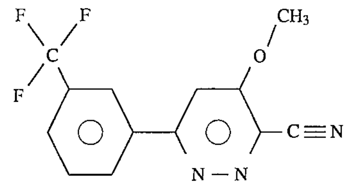 | C 55.92 56.02<br>H 2.89 2.93<br>F 20.41<br>N 15.05 15.10 |
| 78 | 3-PYRIDAZINAMINE, 4-METHOXY-N,N-DIMETHYL-6-[3-(TRIFLUOROMETHYL)PHENYL]- MP: 117.0–119.0 | 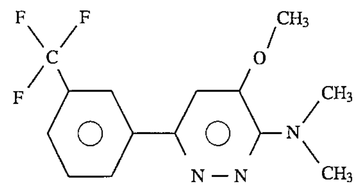 | C 56.56 56.67<br>H 4.75 4.78<br>F 19.17<br>N 14.13 14.11 |
| 79 | PYRIDAZINE, 4-METHOXY-3-(METHOXYSULFINYL)-6-[3-(TRIFLUOROMETHYL)PHENYL]- MP: 169.0–171.0 | 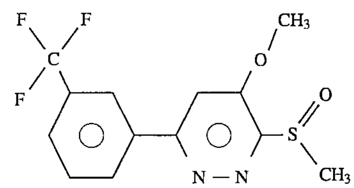 | C 49.36 48.00<br>H 3.51 3.68<br>F 18.02<br>N 8.86 8.61<br>S 10.14 |
| 80 | PYRIDAZINE, 5-(METHYLSULFINYL)-3-[3-(TRIFLUOROMETHYL)PHENYL]- MP: 123.0–125.0 | 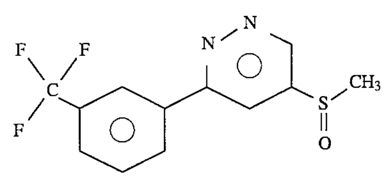 | C 50.35 50.45<br>H 3.17 3.21<br>F 19.91<br>N 9.79 9.77<br>S 11.20 |
| 81 | PYRIDAZINE, 5-METHOXY-3-[3-NITRO-5-(TRIFLUOROMETHYL)PHENYL]-, 1-OXIDE MP: 207.0–209.0 | 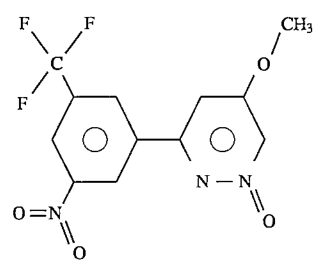 | C 45.73 45.83<br>H 2.56 2.61<br>F 18.08<br>N 13.33 13.24 |
| 82 | PYRIDAZINE, 5-(METHYLSULFONYL)-3-[3-(TRIFLUOROMETHYL)PHENYL]- MP: 196.0–198.0 | 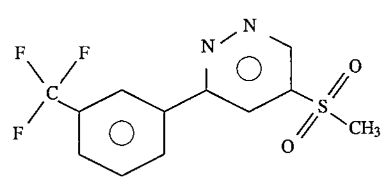 | C 47.68 47.75<br>H 3.00 3.03<br>F 18.86<br>N 9.27 9.27<br>S 10.61 |
| 83 | CARBAMIC ACID, [6-[3-(TRIFLUOROMETHYL)PHENYL]-4-PYRIDAZINYL]-, ETHYL ESTER MP: 204.0–206.0 | 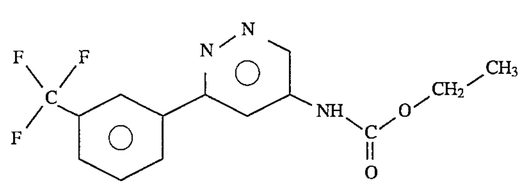 | C 54.02 52.99<br>H 3.89 3.83<br>F 18.31<br>N 13.50 12.95 |

-continued

| Cmp No. | Name | Structure | Analysis (%) Calc'd Found |
|---|---|---|---|
| 84 | 4-PYRIDAZINOL, 6-[3-(TRIFLUOROMETHYL)PHENYL]-, METHANESULFONATE (ESTER) MP: 71.0–73.0 | 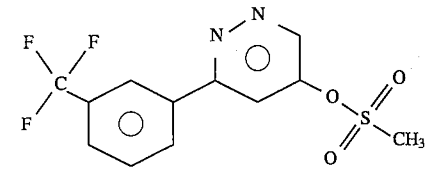 | C 45.28 45.41<br>H 2.85 2.92<br>F 17.91<br>N 8.80 8.69<br>S 10.07 |
| 85 | 3-PYRIDAZINAMINE, N-ETHYL-4-METHOXY-6-[3-(TRIFLUOROMETHYL)PHENYL]- MP: 90.0–92.0 | 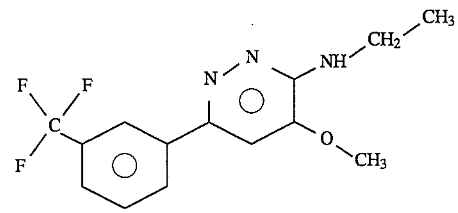 | C 56.56 56.64<br>H 4.75 4.79<br>F 19.17<br>N 14.13 14.19 |
| 86 | 4-PYRIDAZINAMINE, 5-METHOXY-N-METHYL-3-[3-(TRIFLUOROMETHYL)PHENYL]- MP: 124.0–126.0 | 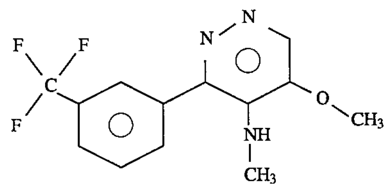 | C 55.12 55.21<br>H 4.27 4.29<br>F 20.12<br>N 14.83 14.89 |
| 87 | PYRIDAZINE, 5-METHOXY-4-(METHYLTHIO)-3-[3-(TRIFLUOROMETHYL)PHENYL]- MP: 52.0–54.0 | 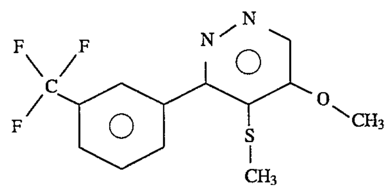 | C 51.99 52.09<br>H 3.69 3.74<br>F 18.98<br>N 9.33 9.24<br>S 10.68 |
| 88 | PYRIDAZINE, 5-METHOXY-4-(METHYSULFONYL)-3-[3-(TRIFLUOROMETHYL)PHENYL]- MP: 125.0–127.0 | 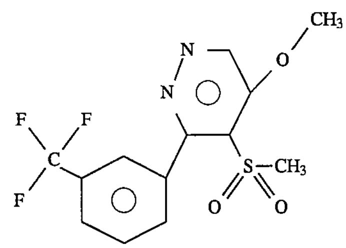 | C 46.99 46.89<br>H 3.34 3.38<br>F 17.15<br>N 8.43 8.38<br>S 9.65 |
| 89 | PYRIDAZINE, 5-METHOXY-4-(METHYLSULFINYL)-3-[3-(TRIFLUOROMETHYL)PHENYL]- MP: 126.0 | 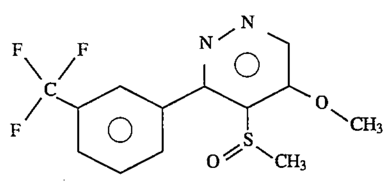 | C 49.36 49.21<br>H 3.51 3.53<br>F 18.02<br>N 8.86 8.77<br>S 10.14 |
| 90 | PYRIDAZINE, 5-METHOXY-4-(METHYLSULFONYL)-3-[3-(TRIFLUOROMETHYL)PHENYL]-, 1-OXIDE MP: 212.0 | 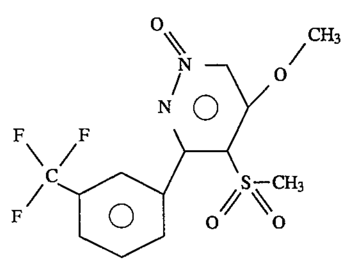 | C 44.83 44.71<br>H 3.18 3.23<br>F 16.36<br>N 8.04 7.97<br>S 9.21 |

-continued

| Cmp No. | Name | Structure | Analysis (%) Calc'd Found |
|---|---|---|---|
| 91 | PYRIDAZINE, 5-METHOXY-3-[3-(TRIFLUOROMETHOXY)PHENYL]- MP: 52.2–52.8 | 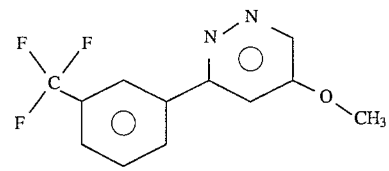 | C 53.34 53.42<br>H 3.36 3.38<br>F 21.09<br>N 10.37 10.30 |
| 92 | PYRIDAZINE, 3-[3-(DIFLUOROMETHYL)PHENYL]-5-METHOXY- MP: 80.0–83.0 | 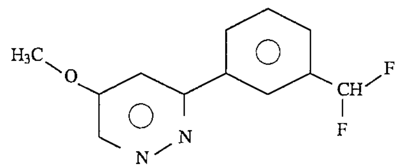 | C 61.01 61.24<br>H 4.27 4.34<br>F 16.09<br>N 11.86 11.46 |
| 93 | 4-PYRIDAZINOL, 5-ETHENYL-6-[3-(TRIFLUOROMETHYL)PHENYL]- MP: 202.0–205.0 | 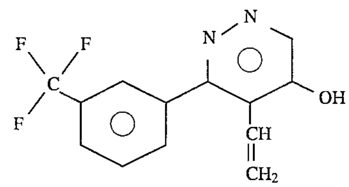 | C 58.65 58.57<br>H 3.41 3.46<br>F 21.41<br>N 10.52 10.43 |
| 94 | PYRIDAZINE, 5-THIOCYANATO-3-[3-(TRIFLUOROMETHYL)PHENYL]- MP: 95.0–97.0 | 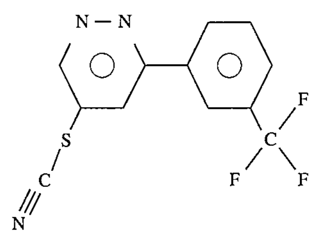 | C 51.24 51.35<br>H 2.15 2.08<br>F 20.27<br>N 14.94 14.99<br>S 11.40 |
| 95 | 4-PYRIDAZINOL, 3-ETHENYL-6-[3-(TRIFLUOROMETHYL)PHENYL]- MP: 215.0–218.0 | 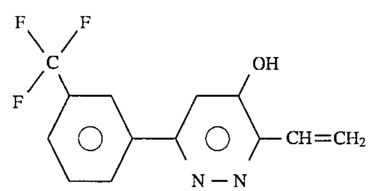 | C 58.65 58.74<br>H 3.41 3.45<br>F 21.41<br>N 10.52 10.45 |
| 96 | 4-PYRIDAZINOL, 5-METHOXY-3-[3-(TRIFLUOROMETHYL)PHENYL]- MP: 255.0 | 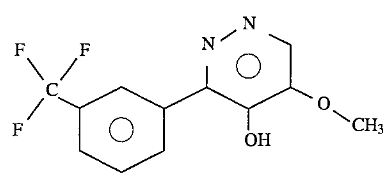 | C 53.34 53.43<br>H 3.36 3.41<br>F 21.09<br>N 10.37 10.29 |
| 97 | 4-PYRIDAZINETHIOL, 6-[3-(TRIFLUOROMETHYL)PHENYL]- MP: 175.0–178.0 | 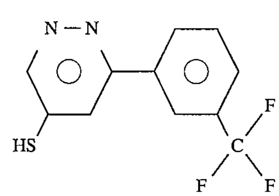 | C 51.56 51.47<br>H 2.75 2.80<br>F 22.24<br>N 10.93 10.87<br>S 12.51 |
| 98 | FURO[2,3-D]PYRIDAZINE, 2,3-DIHYDRO-4-[3-(TRIFLUOROMETHYL)PHENYL]- MP: 108.0–110.0 | 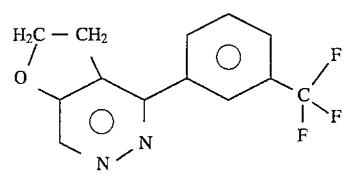 | C 58.65 58.79<br>H 3.41 3.46<br>F 21.41<br>N 10.52 10.41 |

-continued

| Cmp No. | Name | Structure | Analysis (%) Calc'd Found |
|---|---|---|---|
| 99 | PYRIDAZINE, 5-METHOXY-3-[3-METHYL-5-(TRIFLUOROMETHYL)PHENYL]- MP: 101.0–104.0 | 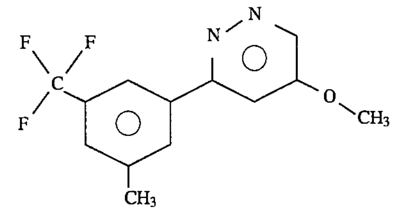 | C 58.21 58.26<br>H 4.13 4.13<br>F 21.25<br>N 10.44 10.38 |
| 100 | PYRIDAZINE, 5-METHOXY-3-[3-(TRIMETHYLSILYL)PHENYL]- MP: 90.0–91.5 | 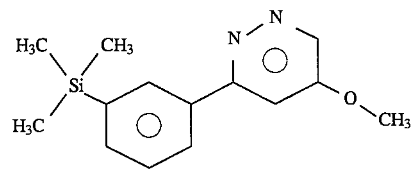 | C 65.07 65.17<br>H 7.02 6.97<br>N 10.84 10.89<br>Si 10.87 |
| 101 | PYRIDAZINE, 5-[(DIFLUOROMETHYL)THIO]-3-[3-(TRIFLUOROMETHYL)PHENYL]- MP: 61.0–63.0 | 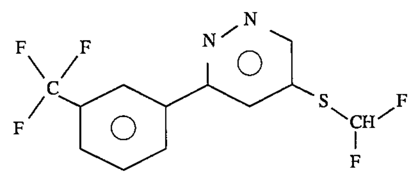 | C 47.06 47.17<br>H 2.30 2.32<br>F 31.02<br>N 9.15 9.20<br>S 10.47 |
| 102 | ACETONITRILE, [[6-[3-(TRIFLUOROMETHYL)PHENYL]-4-PYRIDAZINYL]OXY]- MP: 105.0–107.0 | 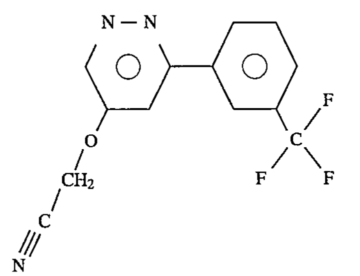 | C 55.92 55.82<br>H 2.89 2.90<br>F 20.41<br>N 15.05 14.99 |
| 103 | 4-PYRIDAZINOL, 6-[3-(TRIFLUOROMETHYL)PHENYL]-, ACETATE (ESTER) MP: 104.0–105.0 | 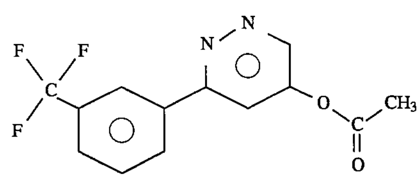 | C 55.33 55.88<br>H 3.21 3.34<br>F 20.20<br>N 9.93 9.72 |
| 104 | FURO[3,2-C]PYRIDAZINE, 6,7-DIHYDRO-7-METHOXY-3-[3-(TRIFLUOROMETHYL)PHENYL]- MP: 105.0–108.0 | 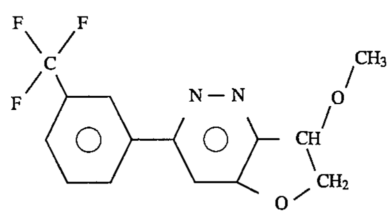 | C 56.76<br>H 3.74<br>F 19.24<br>N 9.46 |
| 105 | FURO[3,2-C]PYRIDAZINE, 7-ETHOXY-6,7-DIHYDRO-3-[3-(TRIFLUOROMETHYL)PHENYL]- MP: 97.0–99.0 | 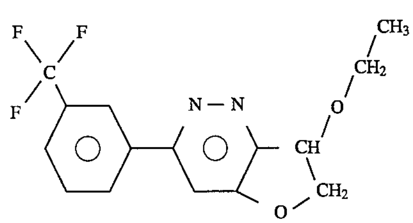 | C 58.06 56.67<br>H 4.22 4.05<br>F 18.37<br>N 9.03 |
| 106 | CARBAMODITHIOIC ACID, DIMETHYL-6-[3-(TRIFLUOROMETHYL)PHENYL]-5-PYRIDAZINYL ESTER MP: 178.0–180.0 | 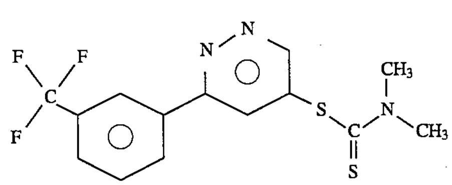 | C 48.97 48.89<br>H 3.52 3.49<br>F 16.60<br>N 12.24<br>S 18.67 |

-continued

| Cmp No. | Name | Structure | Analysis (%) Calc'd Found |
|---|---|---|---|
| 107 | 4-PYRIDAZINAMINE, 5-ETHENYL-6-[3-(TRIFLUOROMETHYL)PHENYL]-<br>MP: 173.0–176.0 | 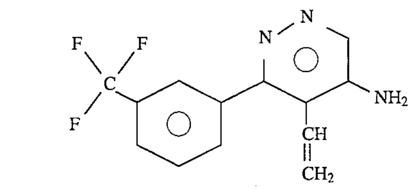 | C 58.87 58.62<br>H 3.80 3.72<br>F 21.49<br>N 15.84 |
| 108 | PYRIDAZINE, 3,4-DIBROMO-6-[3-(TRIFLUOROMETHYL)PHENYL]-<br>MP: 119.0–121.0 | 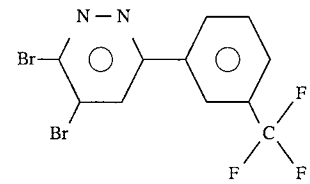 | C 34.59 34.69<br>H 1.32 1.35<br>Br 41.84<br>F 14.92<br>N 7.33 |
| 109 | FURO[3,2-C]PYRIDAZINE, 6,7-DIHYDRO-3-[3-(TRIFLUOROMETHYL)PHENYL]-<br>MP: 147.0–149.0 | 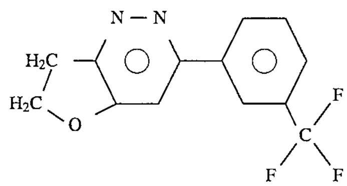 | C 58.65 58.92<br>H 3.41 3.42<br>F 21.41<br>N 10.52 |
| 110 | FURO[3,2-C]PYRIDAZINE, 3-[3-(TRIFLUOROMETHYL)PHENYL]-<br>MP: 157.0–159.0 | 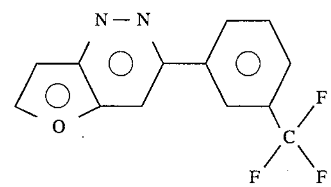 | C 59.10 59.20<br>H 2.67 2.70<br>F 21.57<br>N 10.60 |
| 111 | UREA, N,N-DIMETHYL-N'-[6-[3-(TRIFLUOROMETHYL)PHENYL]-4-PYRIDAZINYL]-<br>MP: 152.0–155.0 | 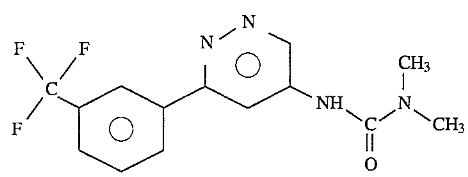 | C 54.19<br>H 4.22<br>F 18.37<br>N 18.06 |
| 112 | PYRIDAZINE, 5-METHOXY-3-[3-[(TRIFLUOROMETHYL)THIO]PHENYL]-<br>MP: 81.0–83.0 | 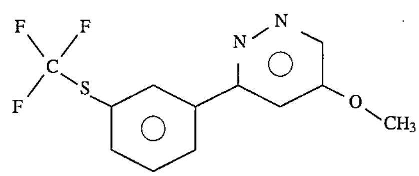 | C 50.35 50.37<br>H 3.17 3.08<br>F 19.91<br>N 9.79<br>S 11.20 |
| 113 | PYRIDAZINE, 3-[3-(1,1-DIMETHYLETHYL)PHENYL]-5-METHOXY-<br>MP: 68.0–70.0 | 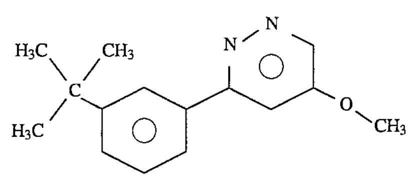 | C 74.35 74.22<br>H 7.49 7.41<br>N 11.56 |
| 114 | PYRIDAZINE, 3-[3-(DIFLUOROMETHOXY)PHENYL]-5-METHOXY-<br>MP: | 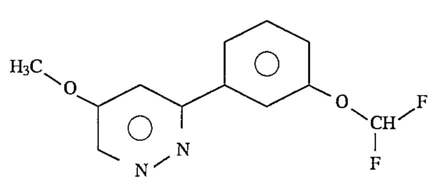 | C 57.14 56.51<br>H 4.00 3.89<br>F 15.07<br>N 11.11 |

| Cmp No. | Name | Structure | Analysis (%) Calc'd Found |
|---|---|---|---|
| 115 | PYRIDAZINE, 5-METHOXY-3-[3-(TRIETHYLSILYL)PHENYL]- MP: 88.5–90.0 | 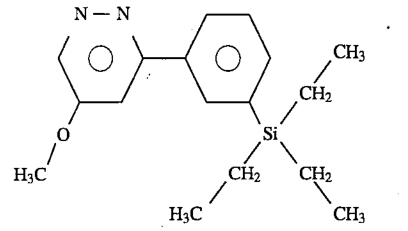 | C 67.95 67.92<br>H 8.05 8.03<br>N 9.32 9.35<br>Si 9.35 |
| 116 | PYRIDAZINE, 3-[3-(DIMETHYLPHENYLSILYL)PHENYL]-5-METHOXY- MP: | 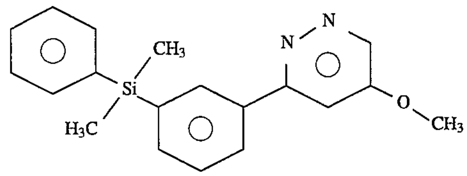 | C 71.21 65.90<br>H 6.29 5.78<br>N 8.74 7.81<br>Si 8.77 |

.15180

PRE-EMERGENT ACTIVITY ON PLANTS

As noted above, compounds of this invention have been found to be effective as herbicides, particularly as pre-emergent herbicides. Table A summarizes results of tests conducted to determine the pre-emergent herbicidal activity of the compounds of this invention. The herbicidal ratings used in Table A were assigned according to a scale based on the percent inhibition of each plant species. The symbol C represents complete control and N or a hyphen represents no data.

One set of pre-emergent tests was conducted as follows:

Topsoil was placed in a pan and compacted to a depth of 0.95 to 1.27 cm from the top of the pan. A predetermined number of seeds of each of several mono-cotyledonous and dicotyledonous annual plant species and/or vegetative propagules of various perennial plant species were placed on top of the soil. The soil required to level fill a pan after seeding or adding vegetative propagules was weighed into another pan. A known amount of the test compound dissolved or suspended in an organic solvent or water and applied in acetone or water as a carrier was thoroughly mixed with this cover soil, and the herbicide/soil mixture was used as a cover layer for the previously prepared pan. In Table A below the amounts of active ingredient were all equivalent to an application rate of 11.2 kilograms/hectare (kg/ha) or other rate as indicated in Table A. After treatment, the pans were moved to a greenhouse bench where they were watered as needed to give adequate moisture for germination and growth.

Approximately 10–14 days (usually 11 days) after planting and treating, the plants were observed and the results recorded.

The plant species usually regarded as weeds which were utilized in one set of pre-emergent activity tests, the data for which are shown in Table A, are identified by letter headings printed above the columns according to the following legend:

COBU—Cocklebur
VELE—Velvetleaf
DOBR—Downy Brome
MOGL—Morningglory
BYGR—Barnyardgrass
ANBG—Annual Bluegrass
SEJG—Seedling Johnsongrass
YENS—Yellow Nutsedge *
INMU—Indian Mustard
WIBW—Wild Buckwheat
 Grown from vegetative propagules

TABLE A

| CP No. | Rate Kg/ha | YENS | ANBG | SEJG | DOBR | BYGR | MOGL | COBU | VELE | INMU | WIBW |
|---|---|---|---|---|---|---|---|---|---|---|---|
| 1 | 11.21 | 0 | 0 | 0 | 0 | 0 | 0 | 0 | 0 | 0 | 0 |
| 2 | 11.21 | 0 | 0 | 0 | 0 | 0 | 0 | 0 | 0 | 0 | 0 |
| 3 | 11.21 | 0 | 0 | 0 | 0 | 0 | 0 | 0 | 0 | N | N |
| 4 | 11.21 | 0 | 20 | 0 | 0 | 10 | 0 | 0 | 0 | 0 | 0 |
| 5 | 11.21 | 60 | C | C | C | C | 90 | 30 | 70 | 90 | 50 |
| 6 | 11.21 | 0 | 10 | 20 | 0 | 20 | 0 | 0 | 0 | 0 | 0 |
| 7 | 11.21 | 10 | 80 | 80 | 0 | 80 | 10 | 10 | 90 | 20 | 0 |
| 8 | 11.21 | 90 | C | C | C | C | C | 90 | C | C | 90 |
| 9 | 11.21 | 0 | 90 | 80 | 20 | 80 | 0 | 0 | 80 | 10 | 0 |
| 10 | 11.21 | 0 | C | 80 | 60 | 90 | 10 | 0 | 10 | 70 | 20 |
| 11 | 11.21 | 0 | 90 | 80 | 20 | 80 | 20 | 0 | 10 | 60 | 0 |
| 12 | 11.21 | 10 | C | C | 90 | C | 30 | 20 | C | 90 | 80 |
| 13 | 11.21 | 0 | 80 | 30 | 20 | 90 | 10 | 0 | 0 | 10 | 0 |
| 14 | 11.21 | 50 | C | C | 90 | C | 70 | 30 | 0 | C | C |
| 15 | 11.21 | 0 | 20 | 70 | 20 | C | 10 | 0 | 10 | 30 | 10 |

TABLE A-continued

| CP No. | Rate Kg/ha | YENS | ANBG | SEJG | DOBR | BYGR | MOGL | COBU | VELE | INMU | WIBW |
|---|---|---|---|---|---|---|---|---|---|---|---|
| 16 | 11.21 | 10 | 20 | 10 | 0 | 70 | 20 | 0 | N | N | N |
|  | 11.21 | 10 | 80 | 70 | 20 | 90 | 60 | 0 | 40 | 50 | 20 |
| 17 | 11.21 | 0 | 0 | 60 | 0 | C | 10 | 0 | 20 | 10 | 0 |
| 18 | 11.21 | 0 | 0 | 0 | 0 | C | 0 | 0 | 0 | 0 | 0 |
| 19 | 11.21 | 0 | 0 | 0 | 0 | 0 | 0 | 0 | 0 | 0 | 0 |
| 20 | 11.21 | 0 | 0 | 0 | 0 | 0 | 0 | 0 | 0 | 0 | 0 |
| 21 | 11.21 | 0 | 0 | 0 | 0 | 0 | 0 | 0 | 0 | 0 | 0 |
| 22 | 11.21 | 0 | 0 | 20 | 10 | 0 | 20 | 0 | 0 | 10 | 0 |
| 23 | 11.21 | 0 | 0 | 20 | 0 | 0 | 10 | 10 | 0 | 0 | 0 |
| 24 | 11.21 | 10 | 0 | 0 | 0 | 50 | 0 | 0 | 0 | 0 | 0 |
| 25 | 11.21 | 0 | 0 | 0 | 0 | 90 | 0 | 0 | 0 | 0 | 0 |
| 26 | 11.21 | 90 | 90 | 90 | C | C | 90 | 90 | C | C | C |
| 27 | 11.21 | 90 | C | C | C | C | 90 | 90 | C | C | 90 |
| 28 | 11.21 | 0 | 10 | 60 | 0 | C | 10 | 0 | 10 | 70 | 40 |
| 29 | 11.21 | 90 | C | C | C | C | C | C | C | C | C |
| 30 | 11.21 | 90 | C | C | C | C | C | C | C | 90 | C |
| 31 | 11.21 | 0 | 90 | 90 | 10 | 50 | 80 | 0 | 50 | 90 | 10 |
| 32 | 11.21 | 30 | 20 | 70 | 20 | 80 | 90 | 0 | 50 | 60 | 10 |
| 33 | 11.21 | 0 | 0 | 0 | 0 | 0 | 0 | 0 | 0 | 0 | 0 |
| 34 | 11.21 | 0 | 0 | 0 | 0 | 0 | 0 | 0 | 0 | 0 | 0 |
| 35 | 11.21 | 0 | 0 | 0 | 0 | 0 | 0 | 0 | 0 | N | N |
| 36 | 11.21 | 0 | 10 | 0 | 0 | 10 | 0 | 0 | 0 | 10 | 10 |
| 37 | 11.21 | 20 | 90 | 90 | 10 | 90 | 80 | 0 | 90 | 90 | 20 |
| 38 | 11.21 | 0 | 0 | 0 | 0 | 0 | 0 | 0 | 0 | 10 | 0 |
| 39 | 11.21 | 0 | 20 | 20 | 0 | 40 | 30 | 0 | C | 60 | 30 |
| 40 | 11.21 | 0 | 30 | 90 | 20 | 70 | 20 | 0 | 90 | 50 | 30 |
| 41 | 11.21 | 0 | 50 | 60 | 20 | 70 | 30 | 0 | 30 | 70 | 10 |
| 42 | 11.21 | 0 | 20 | 40 | 20 | 90 | 50 | 10 | 60 | 70 | 20 |
| 43 | 11.21 | 0 | 0 | 0 | 0 | 0 | 0 | 0 | 0 | 0 | 0 |
| 44 | 11.21 | 0 | 0 | 0 | 0 | 0 | 0 | 0 | 0 | 0 | 0 |
| 45 | 11.21 | 70 | 70 | C | 50 | C | 80 | 50 | 70 | C | 70 |
| 46 | 11.21 | 40 | C | C | 80 | C | 30 | 20 | 90 | C | 90 |
| 47 | 11.21 | 0 | 0 | 0 | 0 | 0 | 0 | 0 | 0 | 0 | 0 |
| 48 | 11.21 | 10 | 90 | C | 80 | C | 80 | 0 | C | 90 | 30 |
| 49 | 11.21 | 80 | 90 | C | 90 | C | C | 70 | C | C | C |
| 50 | 11.21 | 40 | C | C | 80 | C | C | 20 | 50 | C | 10 |
| 51 | 11.21 | 0 | 0 | 0 |  | 0 | 0 | 0 | 10 | 20 | 0 |
| 52 | 11.21 | 0 | 80 | 70 | 10 | 70 | 30 | 0 | 80 | 80 | 70 |
| 53 | 11.21 | 80 | C | C | C | C | C | 30 | 90 | C | C |
| 54 | 11.21 | 10 | 90 | 80 | 50 | C | 40 | 10 | 70 | 90 | 20 |
| 55 | 11.21 | 0 | 0 | 20 | 0 | 0 | 10 | 0 | 0 | 10 | 0 |
| 56 | 11.21 | 0 | 0 | 20 | 0 | 0 | 0 | 0 | 0 | 0 | 0 |
| 57 | 11.21 | 60 | C | C | 90 | C | 80 | 70 | C | C | C |
| 58 | 11.21 | 0 | 0 | 0 | 0 | 60 | 0 | 0 | 0 | 0 | 0 |
| 59 | 11.21 | 20 | 30 | 60 | 10 | 80 | 50 | 0 | 80 | 30 | 10 |
| 60 | 11.21 | 0 | 0 | 10 | 0 | 20 | 0 | 0 | 0 | 10 | 0 |
| 61 | 11.21 | 0 | 0 | 20 | 0 | 0 | 0 | 0 | 0 | 10 | 0 |
| 62 | 11.21 | 0 | 10 | 20 | 30 | 80 | 40 | 10 | 60 | 70 | 10 |
| 63 | 11.21 | 90 | C | C | C | C | C | 90 | C | C | C |
| 64 | 11.21 | 20 | 20 | 70 | 30 | 80 | 20 | 0 | 10 | 60 | 10 |
| 65 | 11.21 | 0 | 90 | 90 | 10 | 90 | 90 | 0 | 90 | 90 | 50 |
| 66 | 11.21 | 20 | 90 | 90 | 20 | 90 | 90 | 0 | 90 | 90 | 30 |
| 67 | 11.21 | 0 | C | 90 | 80 | C | 90 | 0 | 30 | C | 30 |
| 68 | 11.21 | 20 | 80 | C | 20 | C | 80 | 10 | 20 | 90 | 80 |
| 69 | 11.21 | 80 | 90 | C | 30 | C | 70 | 0 | 30 | 90 | 90 |
| 70 | 11.21 | 0 | 30 | 80 | 10 | 90 | 40 | 0 | 0 | 30 | N |
| 71 | 11.21 | 0 | 10 | 80 | 10 | 70 | 50 | 0 | 10 | 50 | 30 |
| 72 | 11.21 | 0 | 40 | 80 | 30 | C | 60 | 70 | 90 | 90 | 20 |
| 73 | 11.21 | 0 | 80 | 90 | 20 | C | 90 | 50 | C | C | 30 |
| 74 | 11.21 | 0 | 0 | 80 | 20 | 20 | 30 | 0 | 50 | 80 | 10 |
| 75 | 11.21 | 0 | 0 | 0 | 0 | 20 | 0 | 0 | 0 | 30 | 0 |
| 76 | 11.21 | 0 | 10 | 40 | 10 | 80 | 70 | 20 | 70 | C | 60 |
| 77 | 11.21 | 0 | 20 | 0 | 0 | 0 | 0 | 0 | 0 | 40 | N |
| 78 | 11.21 | 30 | C | C | 90 | C | C | 60 | C | C | 70 |
| 79 | 11.21 | 0 | 0 | 20 | 0 | 10 | 0 | 0 | 0 | 30 | 0 |
| 80 | 11.21 | 0 | 0 | 20 | 0 | 60 | 20 | 0 | 20 | 30 | 20 |
| 81 | 11.21 | 30 | 20 | 10 | 0 | 60 | 30 | 0 | 10 | 80 | 30 |
| 82 | 11.21 | 0 | 0 | 0 | 0 | 30 | 0 | 0 | 0 | 30 | 0 |
| 83 | 11.21 | 0 | 0 | 0 | 0 | 0 | 0 | 0 | 0 | 0 | 0 |
| 84 | 11.21 | 0 | 0 | 0 | 0 | C | 0 | 0 | 0 | 30 | 0 |
| 85 | 11.21 | 20 | C | 80 | 10 | C | C | 30 | C | C | 50 |
| 86 | 11.21 | 0 | 0 | 0 | 0 | 0 | 0 | 0 | 0 | 0 | 0 |
| 87 | 11.21 | 20 | 30 | 60 | 10 | 80 | 80 | 0 | 20 | 50 | 40 |
| 88 | 11.21 | 0 | 20 | 0 | 0 | 20 | 10 | 0 | 0 | 50 | 20 |
| 89 | 11.21 | 0 | 60 | 60 | 20 | 60 | 30 | 0 | 30 | 80 | 80 |
| 90 | 11.21 | 0 | 0 | 0 | 0 | 0 | 0 | 0 | 0 | 30 | 30 |

TABLE A-continued

| CP No. | Rate Kg/ha | YENS | ANBG | SEJG | DOBR | BYGR | MOGL | COBU | VELE | INMU | WIBW |
|---|---|---|---|---|---|---|---|---|---|---|---|
| 91 | 11.21 | 90 | C | C | C | C | C | C | C | C | C |
| 92 | 11.21 | 80 | C | C | 90 | C | C | 80 | C | C | C |
| 93 | 11.21 | 0 | 0 | 20 | 0 | 30 | 0 | 0 | 0 | 60 | 20 |
| 94 | 11.21 | 20 | 30 | 20 | 0 | 50 | 40 | 0 | 20 | 20 | 0 |
| 95 | 11.21 | 0 | 0 | 0 | 0 | 0 | 0 | 0 | 0 | 0 | 0 |
| 96 | 11.21 | 0 | 0 | 0 | 0 | 20 | 0 | 0 | 0 | 30 | 0 |
| 97 | 11.21 | 0 | 40 | 30 | 20 | 60 | 0 | 0 | 20 | 50 | 30 |
| 98 | 11.21 | 60 | 80 | 80 | 50 | 90 | 90 | 60 | C | C | 70 |
| 99 | 11.21 | 70 | 90 | C | C | C | C | 80 | C | C | 90 |
| 100 | 11.21 | 40 | C | 90 | C | 90 | C | 40 | C | C | C |
| 101 | 11.21 | 40 | C | 80 | 30 | 80 | 30 | 60 | C | C | 80 |
| 102 | 11.21 | 30 | 60 | 30 | 20 | 40 | 0 | 0 | 20 | 60 | 20 |
| 103 | 11.21 | 0 | 0 | 0 | 0 | C | 0 | 0 | 20 | 60 | 40 |
| 104 | 11.21 | 0 | 0 | 0 | 30 | 30 | 50 | 0 | 40 | 80 | 70 |
| 105 | 11.21 | 20 | 90 | 40 | 40 | 70 | 30 | 0 | 80 | 90 | 80 |
| 106 | 11.21 | 0 | 0 | 0 | 0 | 40 | 30 | 0 | 0 | 40 | 30 |
| 107 | 11.21 | 0 | 0 | 0 | 0 | 0 | 0 | 0 | 0 | 0 | 0 |
| 108 | 11.21 | 0 | 0 | 0 | 0 | 0 | 0 | 0 | 0 | 0 | 0 |
| 109 | 11.21 | 0 | 20 | 0 | 0 | 20 | 20 | 20 | 20 | 80 | 20 |
| 110 | 11.21 | 0 | 20 | 20 | 20 | 20 | 70 | 20 | 20 | C | 20 |
| 111 | 5.61 | 0 | 0 | 0 | 0 | 0 | 0 | 0 | 0 | 20 | 0 |
| 112 | 1.12 | 80 | C | C | C | C | C | 40 | C | C | 40 |
| 113 | 11.21 | 60 | C | C | C | C | C | 90 | C | C | C |
| 114 | 11.21 | 70 | C | 70 | 80 | 80 | C | 30 | 90 | 90 | 70 |
| 115 | 11.21 | 0 | 10 | 30 | 20 | 10 | 10 | 10 | 20 | 50 | 10 |
| 116 | 1.00 | 25 | — | — | — | 25 | 0 | 0 | 0 | — | — |

POST-EMERGENT HERBICIDE ACTIVITY ON PLANTS

Although, as has been stated above, the compounds of this invention exhibit predominantly preemergence activity in greenhouse testing, nevertheless many of these compounds are active post-emergent herbicides. The post-emergent activity is best seen on younger plants treated at the 1½ to 2 leaf stage. In the tests which follow, larger and more developed plants were used.

The post-emergence herbicidal activity of compounds of this invention was demonstrated by greenhouse testing, and the results are shown in the following Table B.

Top soil was placed in pans having holes in the bottom and compacted to a depth of 0.95 to 1.27 cm from the top of the pan. A predetermined number of seeds of each of several dicotyledonous and monocotyledonous annual plant species and/or vegetative propagules for the perennial plant species were placed on the soil and pressed into the soil surface. The seeds and/or vegetative propagules were covered with soil and leveled. The pans were then placed on a bench in the greenhouse and watered as needed for germination and growth. After the plants reached the desired age (two to three weeks), each pan (except the control pans) was moved to a spraying chamber and sprayed by means of an atomizer. The spray solution or suspension contained about 0.4% by volume of an emulsifying agent and a sufficient amount of the candidate chemical to give an application rate of the active ingredient of 11.21 kg/ha or other rate as indicated in Table B while applying a total amount of solution or suspension equivalent to 1870 L/ha. The pans were returned to the greenhouse and watered as before and the injury to the plants as compared to those in control pans was observed at approximately 10–14 days (usually 11 days). The plant identifying codes and symbols in Table B are the same as above defined.

TABLE B

| CP No. | Rate Kg/ha | YENS | ANBG | SEJG | DOBR | BYGR | MOGL | COBU | VELE | INMU | WIBW |
|---|---|---|---|---|---|---|---|---|---|---|---|
| 1 | 11.21 | 0 | 0 | 0 | 0 | 10 | 0 | 0 | 0 | 0 | 0 |
| 2 | 11.21 | 0 | 0 | 0 | 0 | 0 | 0 | 0 | 0 | 0 | 0 |
| 3 | 11.21 | 0 | 0 | 0 | 0 | 0 | 0 | 0 | 0 | 0 | 0 |
| 4 | 11.21 | 0 | 0 | 0 | 0 | 0 | 0 | 0 | 0 | 10 | 0 |
| 5 | 11.21 | 0 | 0 | 30 | 10 | 0 | 20 | 10 | 10 | 50 | 10 |
| 6 | 11.21 | 0 | 0 | 20 | 0 | 0 | 0 | 0 | 0 | 20 | 0 |
| 7 | 11.21 | 0 | 0 | 40 | 0 | 20 | 20 | 0 | 0 | 10 | 0 |
| 8 | 11.21 | 40 | C | C | 80 | 90 | 80 | 80 | 90 | 70 | 80 |
|  | 11.21 | 30 | 60 | 60 | 20 | 50 | 50 | 50 | 40 | 30 | 40 |
| 9 | 11.21 | 0 | 20 | 20 | 10 | 10 | 20 | 30 | 20 | 30 | 20 |
| 10 | 11.21 | 0 | 0 | 0 | 0 | 0 | 20 | 20 | 10 | 30 | 10 |
| 11 | 11.21 | 0 | 20 | 30 | 0 | 10 | 30 | 20 | 20 | 40 | 20 |
| 12 | 11.21 | 0 | 30 | 20 | 10 | 30 | 30 | 30 | 30 | 30 | 30 |
|  | 11.21 | 10 | 90 | 10 | 10 | 20 | 30 | 40 | 50 | 90 | 30 |
| 13 | 11.21 | 0 | 0 | 0 | 0 | 0 | 10 | 0 | 0 | 10 | 0 |
| 14 | 11.21 | 10 | 50 | 40 | 20 | 30 | 20 | 30 | 20 | 40 | 20 |
| 15 | 11.21 | 0 | 60 | 70 | 20 | 60 | 50 | 40 | 60 | 60 | 60 |
| 16 | 11.21 | 0 | 10 | 30 | 10 | 30 | 20 | 40 | 30 | 40 | 40 |

TABLE B-continued

| CP No. | Rate Kg/ha | YENS | ANBG | SEJG | DOBR | BYGR | MOGL | COBU | VELE | INMU | WIBW |
|---|---|---|---|---|---|---|---|---|---|---|---|
| 17 | 11.21 | 0 | 10 | 90 | 10 | 20 | 30 | 20 | 20 | 30 | 30 |
| 18 | 11.21 | 0 | 0 | 0 | 0 | 0 | 0 | 0 | 0 | N | N |
| 19 | 11.21 | 0 | 10 | 0 | 0 | 10 | 0 | 0 | 40 | 40 | 20 |
| 20 | 11.21 | 0 | 0 | 0 | 0 | 20 | 30 | 0 | 40 | 30 | 0 |
| 21 | 11.21 | 0 | 0 | 20 | 10 | 0 | 0 | 0 | 20 | 10 | 0 |
| 22 | 11.21 | 0 | 10 | 20 | 10 | 20 | 10 | 30 | 10 | 50 | 20 |
| 23 | 11.21 | 0 | 0 | 0 | 0 | 10 | 0 | 20 | 0 | 30 | 10 |
| 24 | 11.21 | 0 | 0 | 0 | 0 | 0 | 0 | 0 | 0 | 0 | 0 |
| 25 | 11.21 | 0 | 60 | 20 | C | 0 | 20 | 0 | 0 | 0 | 0 |
| 26 | 11.21 | 80 | C | C | 90 | 90 | 80 | 90 | 90 | 90 | C |
| 27 | 11.21 | 60 | 90 | 90 | 90 | 90 | 90 | 90 | 90 | 90 | 90 |
| 28 | 11.21 | 0 | 20 | 20 | 20 | 60 | 30 | 20 | 50 | 50 | N |
| 29 | 11.21 | 50 | C | 90 | C | 90 | 80 | C | C | 90 | C |
| 30 | 11.21 | 30 | C | C | C | 90 | 80 | 90 | C | 80 | C |
| 31 | 11.21 | 0 | 10 | 10 | 0 | 10 | 60 | 40 | 10 | 50 | 20 |
| 32 | 11.21 | 0 | 10 | 20 | 10 | 20 | 30 | 40 | 20 | 50 | 30 |
| 33 | 11.21 | 0 | 30 | 0 | 10 | 20 | 0 | 0 | 0 | 10 | 0 |
| 34 | 11.21 | 0 | 10 | 0 | 0 | 0 | 20 | 0 | 20 | 30 | 10 |
| 35 | 11.21 | 0 | 0 | 0 | 0 | 10 | 20 | 0 | 0 | 10 | 10 |
| 36 | 11.21 | 20 | 20 | 20 | 0 | 20 | 20 | 20 | 20 | 30 | 10 |
| 37 | 11.21 | 0 | 0 | 20 | 0 | 20 | 30 | 30 | 10 | 20 | 10 |
| 38 | 11.21 | 0 | 0 | 10 | 0 | 0 | 30 | 0 | 0 | 20 | 0 |
| 39 | 11.21 | 0 | 20 | 10 | 0 | 0 | 20 | 30 | 30 | 50 | 40 |
| 40 | 11.21 | 20 | 40 | 40 | 30 | 40 | 40 | 40 | 40 | 50 | 60 |
| 41 | 11.21 | 10 | 20 | 10 | 10 | 10 | 20 | 30 | 20 | 30 | 60 |
| 42 | 11.21 | 0 | 30 | 0 | 10 | 30 | 20 | 20 | 0 | 20 | 40 |
| 43 | 11.21 | 0 | 0 | 0 | 0 | 0 | 10 | 0 | 10 | 10 | 10 |
| 44 | 11.21 | 10 | 40 | 90 | 40 | 30 | 60 | 30 | 10 | 20 | 0 |
| 45 | 11.21 | 10 | 10 | 20 | 10 | 20 | 20 | 30 | 20 | 20 | 20 |
| 46 | 11.21 | 10 | 40 | 60 | 20 | 40 | 10 | 40 | 30 | 60 | 40 |
| 47 | 11.21 | 0 | 10 | 10 | 0 | 0 | 0 | 20 | 0 | 40 | 20 |
| 48 | 11.21 | 0 | 40 | 30 | 20 | 10 | 60 | 40 | 30 | 50 | 50 |
| 49 | 11.21 | 30 | 30 | 90 | 10 | 30 | 30 | 40 | 30 | 40 | 80 |
| 50 | 11.21 | 0 | 40 | 40 | 20 | 50 | 80 | 30 | 50 | 70 | 70 |
| 51 | 11.21 | 0 | 0 | 0 | 0 | 30 | 10 | 0 | 10 | 10 | 0 |
| 52 | 11.21 | 0 | 20 | 10 | 0 | 10 | 20 | 30 | 20 | 30 | 20 |
| 53 | 11.21 | 10 | 30 | 40 | 0 | 40 | 60 | 40 | 30 | 40 | 60 |
| 54 | 11.21 | 0 | 10 | 10 | 0 | 10 | 20 | 20 | 20 | 30 | 20 |
| 55 | 11.21 | 0 | 30 | 10 | 0 | 10 | 20 | 20 | 10 | 40 | 20 |
| 56 | 11.21 | 0 | 0 | 0 | 0 | 0 | 0 | 0 | 0 | 0 | 0 |
|  | 11.21 | 0 | 10 | 0 | 0 | 0 | 20 | 20 | 20 | 10 | 10 |
| 57 | 11.21 | 10 | 40 | 20 | 0 | 20 | 30 | 30 | 30 | 50 | 50 |
| 58 | 11.21 | 10 | 0 | 0 | 0 | 10 | 0 | 20 | 0 | 0 | 10 |
| 59 | 11.21 | 10 | 0 | 10 | 0 | 20 | 20 | 30 | 10 | 30 | 30 |
| 60 | 11.21 | 10 | 0 | 20 | 0 | 20 | 10 | 20 | 20 | 30 | 20 |
| 61 | 11.21 | 0 | 20 | 20 | 0 | 20 | 10 | 20 | 20 | 20 | 30 |
| 62 | 11.21 | 0 | 0 | 0 | 0 | 0 | 20 | 0 | 0 | 20 | 0 |
| 63 | 11.21 | 20 | 50 | 50 | 0 | 40 | 60 | 50 | 60 | 70 | 60 |
|  | 11.21 | 20 | C | 80 | 10 | 40 | 80 | 80 | 80 | C | 50 |
| 64 | 11.21 | 0 | 30 | 20 | 0 | 20 | 10 | 30 | 40 | 60 | 60 |
| 65 | 11.21 | 10 | 60 | 80 | 30 | 70 | 80 | 80 | 50 | 60 | 40 |
| 66 | 11.21 | 30 | 30 | 80 | 20 | 40 | 70 | 70 | 30 | 80 | 80 |
| 67 | 11.21 | 0 | 60 | 30 | 30 | 40 | 60 | 40 | 20 | 50 | 30 |
|  | 11.21 | 10 | 90 | 50 | 20 | 50 | 40 | 30 | 30 | 80 | 50 |
| 68 | 11.21 | 0 | 30 | C | 30 | 60 | 40 | 60 | 60 | 80 | 90 |
| 69 | 11.21 | 0 | 30 | 0 | 10 | 30 | 40 | 20 | 30 | 40 | 90 |
| 70 | 11.21 | 0 | 20 | 0 | 10 | 10 | 20 | 0 | 0 | 20 | 30 |
| 71 | 11.21 | 0 | 20 | 0 | 10 | 0 | 10 | 0 | 0 | 30 | 10 |
| 72 | 11.21 | 0 | 10 | 0 | 20 | 0 | 30 | 20 | 10 | 30 | 20 |
| 73 | 11.21 | 0 | 90 | C | 90 | 90 | 80 | 70 | 90 | 90 | 20 |
| 74 | 11.21 | 0 | 10 | 20 | 20 | 10 | 10 | 0 | N | 80 | 10 |
| 75 | 11.21 | 0 | 0 | 0 | 0 | 0 | 0 | 0 | N | 0 | 0 |
| 76 | 11.21 | 0 | 0 | 20 | 20 | 20 | 20 | 20 | 20 | 90 | 50 |
| 77 | 11.21 | 0 | 0 | 20 | 10 | 20 | 90 | 30 | 20 | 60 | 30 |
| 78 | 11.21 | 0 | 90 | 90 | 50 | 80 | 80 | 60 | 90 | 90 | 70 |
| 79 | 11.21 | 20 | 0 | 40 | 20 | 40 | 30 | 40 | 40 | 80 | 60 |
| 80 | 11.21 | 0 | 60 | 60 | 20 | 20 | 60 | 30 | 30 | 80 | 10 |
| 81 | 11.21 | 0 | 20 | 0 | 20 | 0 | 30 | 20 | 10 | 60 | 10 |
| 82 | 11.21 | 0 | 0 | 10 | 10 | 20 | 30 | 20 | 20 | 20 | 0 |
| 83 | 11.21 | 0 | 0 | 0 | 0 | 0 | 0 | 0 | 0 | 0 | 0 |
| 84 | 11.21 | 0 | 0 | 0 | 0 | 0 | 0 | 0 | 0 | 10 | 0 |
| 85 | 11.21 | 10 | 80 | 50 | 30 | 60 | 60 | 60 | 60 | 90 | 80 |
| 86 | 11.21 | 0 | 20 | 30 | 30 | 30 | 30 | 30 | 30 | 20 | 0 |
| 87 | 11.21 | 10 | 40 | 40 | 30 | 40 | 40 | 30 | 30 | 40 | 60 |
| 88 | 11.21 | 0 | 10 | 10 | 0 | 10 | 10 | 10 | 0 | 50 | N |
| 89 | 11.21 | 0 | 40 | 20 | 10 | 50 | 40 | 50 | 30 | 50 | N |

TABLE B-continued

| CP No. | Rate Kg/ha | YENS | ANBG | SEJG | DOBR | BYGR | MOGL | COBU | VELE | INMU | WIBW |
|---|---|---|---|---|---|---|---|---|---|---|---|
| 90 | 11.21 | 0 | 0 | 0 | 0 | 0 | 10 | 10 | 0 | 30 | N |
| 91 | 11.21 | 20 | 80 | 90 | 50 | 80 | 80 | 70 | 60 | 50 | 90 |
| 92 | 11.21 | 10 | 30 | 60 | 20 | 20 | 30 | 30 | 40 | 40 | 90 |
| 93 | 11.21 | 0 | 30 | 30 | 20 | 10 | 20 | 20 | 10 | 50 | 30 |
| 94 | 11.21 | 0 | 10 | 10 | 0 | 30 | 20 | 10 | 10 | 10 | 0 |
| 95 | 11.21 | 0 | 0 | 0 | 0 | 0 | 0 | 0 | 0 | 0 | 0 |
| 96 | 11.21 | 0 | 0 | 0 | 0 | 0 | 0 | 0 | 0 | 0 | 0 |
| 97 | 11.21 | 0 | 0 | 0 | 10 | 10 | 0 | 10 | 20 | 30 | 20 |
| 98 | 11.21 | 0 | 60 | 30 | 40 | 20 | 10 | 30 | 20 | 50 | 90 |
| 99 | 11.21 | 30 | 90 | 70 | 30 | 90 | 80 | 80 | 60 | 90 | C |
| 100 | 11.21 | 10 | 50 | 70 | 40 | 80 | 80 | 70 | 80 | 70 | 80 |
| 101 | 11.21 | 0 | 20 | 10 | 10 | 10 | 0 | 30 | 20 | 40 | 30 |
| 102 | 11.21 | 0 | 10 | 10 | 20 | 20 | 20 | 40 | 20 | 50 | 30 |
| 103 | 11.21 | 0 | 0 | 0 | 0 | 0 | 10 | 0 | 0 | 0 | 0 |
| 104 | 11.21 | 0 | 0 | 0 | 0 | 10 | 10 | 0 | 20 | 60 | N |
| 105 | 11.21 | 0 | 0 | 0 | 0 | 0 | 0 | 0 | 10 | 10 | 30 |
| 106 | 11.21 | 0 | 0 | 0 | 0 | 0 | 0 | 0 | 0 | 10 | 0 |
| 107 | 11.21 | 0 | 0 | 0 | 0 | 0 | 0 | 0 | 0 | 0 | 0 |
| 108 | 11.21 | 0 | 0 | 20 | 20 | 20 | 0 | 0 | 0 | 0 | 0 |
| 109 | 11.21 | 0 | 0 | 0 | 0 | 0 | 0 | 0 | 20 | 0 | 0 |
| 110 | 11.21 | 0 | 0 | 0 | 0 | 0 | 0 | 0 | 0 | 30 | 0 |
| 111 | 5.61 | 0 | 0 | 0 | 0 | 0 | 0 | 0 | 0 | 20 | 0 |
| 112 | 1.12 | 20 | 60 | 70 | 20 | 80 | 70 | 70 | 70 | 50 | 80 |
| 113 | 11.21 | 30 | C | C | 60 | 90 | 70 | 70 | 80 | 70 | 90 |
|  | 11.21 | 10 | C | C | C | C | C | 89 | C | C | C |
| 114 | 11.21 | 10 | 30 | 70 | 10 | 30 | 80 | 70 | 60 | 30 | 30 |
| 115 | 11.21 | 0 | 10 | 30 | 10 | 10 | 30 | 70 | 60 | 20 | 10 |
| 116 | 1.00 | 0 | — | — | — | 0 | 35 | 55 | 50 | — | — |

As can be seen from the data above, some of the compounds are suitably safe on certain crops and can thus be used for selective control of weeds in these crops. Known safehers can be added to the formulated herbicidal formulation when additional crop safening is indicated.

The methods of making such compositions are well known. Solutions are prepared by simply mixing the ingredients to be included therein. Fine solid compositions are made by blending and, usually, grinding as in a hammer or fluid energy mill. Suspensions are prepared by wet milling, for example. Granules and pellets can be made by spraying the material containing the active material upon preformed granular carriers or by agglomeration techniques or the like.

The herbicidal compositions of this invention, including concentrates which require dilution prior to application, may contain at least one active ingredient and an adjuvant in liquid or solid form. The compositions are prepared by admixing the active ingredient with an adjuvant including diluents, extenders, carriers, and conditioning agents to provide compositions in the form of finely-divided particulate solids, granules, pellets, solutions, dispersions or emulsions. Thus, it is believed that the active ingredient could be used with an adjuvant such as a finely-divided solid, a liquid of organic origin, water, a wetting agent, a dispersing agent, an emulsifying agent or any suitable combination of these.

Suitable wetting agents include alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, ditertiary acetylenic glycols, polyoxyethylene derivatives of alkylphenols (particularly isooctylphenol and nonylphenol) and polyoxyethylene derivatives of the mono-higher fatty acid esters of hexitol anhydrides (e.g., sorbitan). Preferred dispersants are methyl cellulose, polyvinyl alcohol, sodium lignin sulfonates, polymeric alkyl naphthalene sulfonates, sodium naphthalene sulfonate and polymethylene bisnaphthalene sulfonate.

Wettable powders are water-dispersible compositions containing one or more active ingredients, an inert solid extender and one or more wetting and dispersing agents. The inert solid extenders are usually of mineral origin such as the natural clays, diatomaceous earth and synthetic minerals derived from silica and the like. Examples of such extenders include kaolinites, attapulgite clay and synthetic magnesium silicate. The wettable powders and compositions of this invention usually contain from about 0.5 to 60 parts (preferably from 5–20 parts) of active ingredient, from about 0.25 to 25 parts (preferably 1–15 parts) of wetting agent, from about 0.25 to 25 parts (preferably 1.0–15 parts) of dispersant and from 5 to about 95 parts (preferably 5–50 parts) of inert solid extender, all parts being by weight of the total composition. Where required, from about 0.1 to 2.0 parts of the solid inert extender can be replaced by a corrosion inhibitor or anti-foaming agent or both.

Other formulations include dust concentrates comprising from 0.1 to 60% by weight of the active ingredient on a suitable extender; these dusts may be diluted for application at concentrations within the range of from about 0.1–10% by weight.

Aqueous suspensions or emulsions may be prepared by stirring a nonaqueous solution of a water-insoluble active ingredient and an emulsification agent with water until uniform and then homogenizing to give stable emulsions of very finely-divided particles. The resulting concentrated aqueous suspension is charactertzed by its extremely small particle size, so that when diluted and sprayed, coverage is very uniform. Suitable concentrations of these formulations contain from about 0.1–60% preferably 5–50% by weight of active ingredient, the upper limit being determined by the solubility limit of active ingredient in the solvent.

Concentrates are usually solutions of active ingredient in water-immiscible or partially water-immiscible solvents, together with a surface active agent. Suitable solvents for the active ingredient of this invention include N,N-dimethylformamide, dimethyl-sulfoxide, N-methyl-pyrrolidone, hydrocarbons and water-immiscible ethers, esters or ketones. However, other high strength liquid concentrates may be formulated by dissolving the active ingredient in a solvent then diluting, e.g., with kerosene, to spray concentration.

The concentrate compositions herein generally contain from about 0.1 to 95 parts (preferably 5–60 parts) active ingredient, about 0.25 to 50 parts (preferably 1–25 parts) surface active agent and where required about 4 to 94 parts solvent, all parts being by weight based on the total weight of emulsifiable oil.

Granules are physically stable particulate compositions comprising at least one active ingredient adhered to or distributed through a basic matrix of an inert, finely-divided particulate extender. In order to aid leaching of the active ingredient from the particulate, a surface active agent such as those listed hereinbefore can be present in the composition. Natural clays, pyrophyllites, illits, and vermiculite are examples of operable classes of particulate mineral extenders. The preferred extenders are the porous, absorptive, preformed particles such as preformed and screened particulate attapulgite clay or heat expanded, particulate vermiculite and the finely-divided clays such as kaolin clays, hydrated attapulgite or bentonitic clays. These extenders are sprayed or blended with the active ingredient to form the herbicidal granules.

The granular compositions of this invention may contain from about 0.1 to about 30 parts by weight of active ingredient per 100 parts by weight of clay and 0 to about 5 parts by weight of surface active agent per 100 parts by weight of particulate clay.

The compositions of this invention can also contain other additaments, for example, fertilizers, other herbicides, other pesticides, safehers and the like used as adjuvants or in combination with any of the above-described adjuvants. Chemicals useful in combination with the active ingredients of this invention include, for example, triazines, ureas, carbamates, acetamides, acetanilides, uracils, acetic acid or phenol derivatives, thiolcarbamates, triazoles, benzoic acids, nitriles, biphenyl ethers and the like, such as:

Heterocyclic Nitrogen/Sulfur Derivatives

2-Chloro-4-ethylamino-6-isopropylamino-s-triazine
2-Chloro-4,6-bis(isopropylamino)-s-triazine
2-Chloro-4,6-bis(ethylamino)-s-triazine
3-Isopropyl-1H-2,1,3-benzothiadiazin-4-(3H)-one 2,2-dioxide
3-Amino-1,2,4-triazole
6,7-Dihydrodipyrido (1,2-d:α',1'-c)-pyrazidiinium salt
5-Bromo-3-isopropyl-6-methyluracil 1,1'-dimethyl-4,4'-bipyridinium
2-(4-isopropyl-4-methyl-5-oxo-2-imidazolin-2-yl)-3-quinolinecarboxylic acid
Isopropylamine salt of 2-(4-isopropyl-4-methyl-5-oxo-2-imidazolin-2-yl)nicotinic acid
Methyl 6-(4-isopropyl-4-methyl-5-oxo-2-imidazolin-2-yl)-m-toluate and methyl 2-(4-isopropyl-4-methyl-5-oxo-2-imidazolin-2-yl)-p-toluate Ureas N-(4-chlorophenoxy)phenyl-N,N-dimethylurea
N,N-dimethyl-N'-(3-chloro-4-methylphenyl)urea
3-(3,4-Dichlorophenyl)-1,1-dimethylurea
1,3-Dimethyl-3-(2-benzothiazolyl)urea
3-(p-Chlorophenyl)-1,1-dimethylurea
1-Butyl-3-(3,4-dichlorophenyl)-1-methylurea
2-Chloro-N[(4-methoxy-6-methyl-3,5-triazin-2-yl)aminocarbonyl]-benzenesulfonamide
Methyl-2-(((((4,6-dimethyl-2-pyrimidinyl)amino)carbonyl)amino)sulfonyl)benzoate
Ethyl 2-[methyl 2-(((((4,6-dimethyl-2-pyrimidinyl)amino)carbonyl)amino)sulfonyl)]benzoate
Methyl-2((4,6-dimethoxy pyrimidin-2-yl)aminocarbonyl)amino sulfonyl methyl)benzoate
Methyl 2-(((((4-methoxy-6-methyl-1,3,5-triazin-2-yl)amino)carbonyl)amino)sulfonyl)benzoate Carbamates/Thiolcarbamates 2-Chloroallyl diethyldithiocarbamate
S-(4-Chlorobenzyl)N,N-diethylthiolcarbamate
Isopropyl N-(3-chlorophenyl)carbamate
S-2,3-Dichloroallyl N,N-diisopropylthiolcarbamate
S-N,N-dipropylthiolcarbamate
S-Propyl N,N-dipropylthiolcarbamate
S-2,3,3-Trichloroallyl N,N-diisopropylthiolcarbamate Acetamides/Acetanilides/Anilines/Amides 2-Chloro-N,N-dial lylacetamide
N,N-dimethyl-2,2-diphenylacetamide
N-(2,4-dimethyl-5-[[(trifluoromethyl)sulfonyl]amino]phenyl]acetamide N-isopropyl-2-chloroacetanilide
2',6'-Diethyl-N-methoxymethyl-2-chloroacetanilide
2'-Methyl-6'-ethyl-N-(2-methoxypropyl-2-yl)-2-chloroacetanilide
α,α,α-Trifluoro-2,6-dinitro-N,N-dipropyl-p-toluidine
N-(1,1-dimethylpropynyl)-3,5-dichlorobenzamide Acids/Esters/Alcohols 2,2-Dichloropropionic acid
2-Methyl-4-chlorophenoxyacetic acid
2-Dichlorophenoxyacetic acid
Methyl-2-[4-(2,4-dichlorophenoxy)phenoxy]propionate
3-Amino-2,5-dichlorobenzoic acid
2-Methoxy-3,6-dichlorobenzoic acid
2,3,6-Trichlorophenylacetic acid
N-1-naphthylphthalamic acid
Sodium 5-[2-chloro-4-(trifluoromethyl)phenoxy]-2-nitrobenzoate
4,6-Dinitro-o-sec-butylphenol N-(phosphonomethyl)glycine and its salts
Butyl 2-[4-[[5-(trifluoromethyl)-2-pyridinyl]oxy]phenoxy] propanoate Ethers 2,4-Dichlorophenyl-4-nitrophenyl ether
2-Chloro-α,α,α-trifluoro-p-tolyl-3-ethoxy-4-nitrodiphenyl ether
5-(2-Chloro-4-trifluoromethylphenoxy)-N-methyl sulfonyl-2-nitrobenzamide
1'-(Carboethoxy)ethyl 5-[2-chloro-4-(trifluoromethyl)phenoxy]-2-nitrobenzoate Miscellaneous 2,6-Dichlorobenzonitrile
Monosodium acid methanearsonate
Disodium methanearsonate
2-(2-chlorophenyl)methyl-4,4-dimethyl-3-isoxazolidinone
7-Oxabicyclo(2.2.1)heptane, 1-methyl-4-(1-methylethyl)-2-(2-methylphenylmethoxy)-, exo Fertilizers useful in combination with the active ingredients include, for example, ammonium nitrate, urea, potash and superphosphate. Other useful additaments include materials in which plant organisms take root and grow such as compost, manure, humus, sand and the like.

Herbicidal formulations of the types described above are exemplified in several illustrative embodiments below.

| | | Weight Percent |
|---|---|---|
| I. Emulsifiable Concentrates | | |
| A. | Compound of Example No. 13 | 11.0 |
| | Free acid of complex organic phosphate or aromatic or aliphatic hydrophobe base (e.g., GAFAC RE-610, registered trademark of GAF Corp.) | 5.59 |
| | Polyoxyethylene/polyoxypropylene block copolymer with butanol (e.g., Tergitol XH, registered trademark of Union Carbide Corp.) | 1.11 |
| | Phenol | 5.34 |
| | Monochlorobenzene | 76.96 |
| | | 100.00 |
| B. | Compound of Example No. 23, | 25.00 |
| | Free acid of complex organic phosphate or aromatic of aliphatic hydrophobe base (e.g., GAFAC RE-610) | 5.00 |
| | Polyoxyethylene/polyoxyproplene block copolymer with butanol (e.g., Tergitol XH) | 1.60 |
| | Phenol | 4.75 |
| | Monochlorobenzene | 63.65 |
| | | 100.00 |
| II. Flowables | | |
| A. | Compound of Example No. 12 | 25.00 |
| | Methyl cellulose | 0.3 |
| | Silica Aerogel | 1.5 |
| | Sodium lignosulfonate | 3.5 |
| | Sodium N-methyl-N-oleyl taurate | 2.0 |
| | Water | 67.7 |
| | | 100.00 |
| B. | Compound of Example No. 4 | 45.0 |
| | Methyl cellulose | 0.3 |
| | Silica aerogel | 1.5 |
| | Sodium lignosulfonate | 3.5 |
| | Sodium N-methyl-N-oleyl taurate | 2.0 |
| | Water | 47.7 |
| | | 100.00 |
| III. Wettable Powders | | |
| A. | Compound of Example No. 16 | 25.0 |
| | Sodium lignosulfonate | 3.0 |
| | Sodium N-methyl-N-oleyl-tuarate | 1.0 |
| | Amorphous silica (synthetic) | 71.0 |
| | | 100.00 |
| B. | Compound of Example 20 | 80.00 |
| | Sodium dioctyl sulfosuccinate | 1.25 |
| | Calcium lignosulfonate | 2.75 |
| | Amorphous silica (synthetic) | 16.00 |
| | | 100.00 |
| C. | Compound of Example No. 6 | 10.0 |
| | Sodium lignosulfonate | 3.0 |
| | Sodium N-methyl-N-oleyl-taurate | 1.0 |
| | Kaolinte clay | 86.0 |
| | | 100.00 |
| IV. Dusts | | |
| A. | Compound of Example No. 11 | 2.0 |
| | Attapulgite clay | 98.0 |
| | | 100.00 |
| B. | Compound of Example No. 8 | 60.0 |
| | Montmorillonite | 40.0 |
| | | 100.00 |
| *-continued* | | Weight Percent |
| C. | Compound of Example No. 19 | 30.0 |
| | Ethylene glycol | 1.0 |
| | Bentonite | 69.0 |
| | | 100.00 |
| D. | Compound of Example No. 13 | 1.0 |
| | Diatomaceous earth | 99.0 |
| | | 100.00 |
| V. Granules | | |
| A. | Compound of Example No. 6 | 15.0 |
| | Granular attapulgite (20/40 mesh) | 85.0 |
| | | 100.00 |
| B. | Compound of Example No. 7 | 30.0 |
| | Diatomaceous earth (20/40) | 70.0 |
| | | 100.00 |
| C. | Compound of Example No. 8 | 1.0 |
| | Ethylene glycol | 5.0 |
| | Methylene blue | 0.1 |
| | Pyrophyllite | 93.9 |
| | | 100.00 |
| D. | Compound of Example No. 9 | 5.0 |
| | Pyrophyllite (20/40) | 95.0 |
| | | 100.00 |

When operating in accordance with the present invention, effective amounts of the compounds of this invention are applied to the soil containing the seeds, or vegetative propagules or may be incorporated into soil media in any convenient fashion. The application of liquid and particulate solid compositions to the soil can be carried out by conventional methods, e.g., power dusters, boom and hand sprayers and spray dusters. The compositions can also be applied from airplanes as a dust or a spray because of their effectiveness at low dosages.

The exact amount of active ingredient to be employed is dependent upon various factors, including the plant species and stage of development thereof, the type and condition of soil, the amount of rainfall and the specific compounds employed. In selective preemergence application or to the soil, a dosage of from about 0.02 to about 11.2 kg/ha, preferably from about 0.1 to about 5.60 kg/ha, is usually employed. Lower or higher rates may be required in some instances. One skilled in the art can readily determine from this specification, including the above examples, the optimum rate to be applied in any particular case.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

What is claimed is:

1. 2-(1-(3-trifluoromethyl)phenyl)ethylidene hydrazine carboxylic acid.

* * * * *